(12) United States Patent
Fujita et al.

(10) Patent No.: US 6,533,911 B1
(45) Date of Patent: Mar. 18, 2003

(54) DEVICE FOR MEASURING COMBUSTIBLE-GAS CONCENTRATION IN AN EXHAUST GAS

(75) Inventors: Hiroki Fujita, Aichi (JP); Shoji Kitanoya, Aichi (JP); Kenji Kato, Aichi (JP); Tomohiro Fuma, Aichi (JP); Ryuji Inoue, Gifu (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/590,189

(22) Filed: Jun. 9, 2000

(30) Foreign Application Priority Data

Jun. 10, 1999 (JP) .......................................... 11-164520
Aug. 2, 1999 (JP) .......................................... 11-219351

(51) Int. Cl.$^7$ ............................................. G01N 27/407
(52) U.S. Cl. ...................... 204/424; 204/426; 204/429; 73/23.31
(58) Field of Search ..................... 204/424–429, 204/290.08, 290.14; 205/785, 787; 73/23.31

(56) References Cited

U.S. PATENT DOCUMENTS

| | | | |
|---|---|---|---|
| 4,720,335 A | * 1/1988 | Fukushima et al. | 204/424 |
| 5,326,597 A | * 7/1994 | Sawada et al. | 427/448 |
| 5,472,580 A | * 12/1995 | Kennard, III et al. | 204/421 |
| 5,762,771 A | * 6/1998 | Yamada et al. | 204/428 |
| 5,833,836 A | * 11/1998 | Takami et al. | 205/785 |
| 5,875,768 A | 3/1999 | Schenk et al. | |
| 5,989,624 A | * 11/1999 | Kida et al. | 427/125 |

FOREIGN PATENT DOCUMENTS

| | | |
|---|---|---|
| DE | 2304464 C2 | 3/1983 |
| EP | 0 851 226 A2 | 7/1998 |
| JP | 10-82763 | 3/1998 |
| WO | WO 95/25277 | 9/1995 |

OTHER PUBLICATIONS

Lukacs et al., Solid State Ionics 68 (1994) 93–98, month N/A.*

* cited by examiner

Primary Examiner—Robert J. Warden, Sr.
Assistant Examiner—Kaj K. Olsen
(74) Attorney, Agent, or Firm—Sughrue Mion, PLLC

(57) ABSTRACT

A device and method for measuring combustible-gas concentration and a device and method for measuring hydrocarbon-gas concentration, which exhibit low dependence on oxygen concentration variations as well as low temperature dependence. Paste is applied to the inner surface of a closed-bottom cylindrical solid electrolyte element, thereby forming a layer serving as a reference electrode. Plating with platinum is performed, so as to form a layer serving as a first detection electrode, on the outer surface of the solid electrolyte element only at a portion extending from an end portion of the solid electrolyte element to the vicinity of the interface between a heating resistor and a heating-resistor lead portion, which are formed within a heater element contained in the cylindrical solid electrolyte element. Paste which contains gold powder and 10 parts of indium oxide is applied onto the platinum-plating layer so as to form a layer serving as a second detection electrode, followed by firing. Subsequently, a diffusion layer containing spinel is formed by thermal spraying on the surface of a detection electrode. The heater element is disposed in the solid electrolyte element such that an end portion abuts an inner bottom portion of the solid electrolyte element. Lead wires for measuring internal resistance, which extend from the reference electrodes, and a lead wire extending from the detection electrode are connected to a temperature controller.

17 Claims, 12 Drawing Sheets

DEVICE FOR MEASURING COMBUSTIBLE-GAS CONCENTRATION IN AN EXHAUST GAS

BACKGROUND OF THE INVENTION

1. Field of the Invention

The present invention relates to a device for measuring combustible-gas concentration and a method for measuring combustible-gas concentration by use of the device. More particularly, the invention relates to such devices and methods capable of measuring the concentration of a combustible gas such as hydrocarbon gas contained in an exhaust gas emitted from a lean-burn engine including a diesel engine.

The present device enables measurement of the combustible gas concentration with low dependency on the high concentration of oxygen contained in such a lean-burn engine.

2. Description of the Related Art

Conventionally, in order to optimize the combustion efficiency of an internal combustion engine and to maximize combustion of combustible gases contained in a combustion exhaust gas, a percentage of a gas component, particularly oxygen, contained in the combustion exhaust gas is measured, and the measured data is fed back to an engine control system. However, in order to cope with a trend toward tightening of exhaust gas regulations and a goal of attaining fuel economy in recent years, there have been demands for more sensitive detection of a combustible gas component contained in the exhaust gas in addition to apparatus and methods for accurately measuring concentration of the combustible gas component.

For example, since the lean-bum engine can promote fuel economy but emits a large amount of nitrogen oxides, a system has been studied as shown in FIG. 1 for eliminating nitrogen oxides, in which system the fuel is added into the exhaust gas by an injector placed at a position upstream of a catalytic converter. Also, there have been demands for attachment of a catalyst to the diesel engine that is conventionally unequipped with a catalytic converter. Thus, a sensor system as shown in FIGS. 2 or 3 has been studied, which is capable of measuring the concentration of a combustible gas and/or detecting deterioration of the catalytic converter used therein.

However, a lean-bum engine involves great variations in oxygen concentration as compared to a conventional stoichiometricly controlled engine and exhibits a particularly high oxygen concentration under lean conditions. Thus, there have been demands for a device for measuring combustible-gas concentration capable of detecting a hydrocarbon that contains a relatively large number of carbon atoms (about 2–15 carbon atoms), without dependence on oxygen concentration.

Techniques for detecting such a combustible gas are disclosed in PCT Application Laid-open No. WO 95/25277 and Japanese Patent Application Laid-Open (kokai) No. 82763/1998. According to the former publication, a detection electrode may contain gold, silver, platinum, or bismuth. The latter publication does not particularly describe a detection electrode. These publications do not mention techniques that decrease a measurement problem such as dependence on oxygen concentration and/or dependence on temperature of the exhaust gas.

SUMMARY OF THE INVENTION

It is therefore an object of the present invention to solve the above-mentioned problems of the prior art, and to provide a device for measuring combustible-gas concentration and a method for measuring combustible-gas concentration using of the same. This device and method enables sensitive detection of a combustible gas such as a hydrocarbon gas, and accurate detection of concentration of such a combustible gas while suppressing dependence on oxygen concentration in a combustion exhaust gas and/or dependence on temperature of a gas to be measured, and as well exhibiting a stable response.

A device of a first aspect of the invention for measuring combustible-gas concentration comprises an oxygen-ion-conductive solid electrolyte element, a reference electrode and a detection electrode formed on the surface of the solid electrolyte element, and a heater element for heating the solid electrolyte element. The device is characterized in that the detection electrode contains gold and a metallic oxide. The "metallic oxide" may be an oxide of a transition metal. Preferably, the detection electrode contains an oxide of at least one element selected from among In, Fe, Ta, Ga, Sr, Eu, W, Ce, Ti, Zr and Sn. Most preferably, the detection electrode contains one of indium oxide and iron oxide. The metallic oxide greatly reduces dependence on oxygen concentration of the device for measuring combustible-gas concentration, according to the invention.

Examples of the above-mentioned "combustible gas" include hydrocarbons contains 2–15 carbon atoms, hydrogen, carbon monoxide and ammonia. The above-mentioned "solid electrolyte element" may be a known oxygen-ion-conductive solid electrolyte body such as a zirconia-based ceramic body and an $LaGaO_3$-based ceramic body.

The above-mentioned "reference electrode" is an electrode which is brought into contact with a reference gas or an oxygen atmosphere of constant pressure established by means of an oxygen pump. The reference electrode shows a higher electric potential than does a detection electrode upon contact with a combustible gas component contained in the gas being measured.

The above-mentioned "detection electrode" is an electrode exposed to the gas to be measured.

The above-mentioned "heater element" is an element for heating the solid electrolyte element so as to maintain the solid electrolyte element at a predetermined temperature, and may assume a conventional form and may be formed from a known material. In the case where the above-mentioned "solid electrolyte element" assumes the form of a closed-bottomed cylinder with a hollow inside, the heater element may assume a rod form, such as the form of a round bar or strap, so as to be placed in the hollow . In the case where the device for measuring combustible-gas concentration assumes the form of a laminate, the heater element may be an integral portion of the laminate or may be disposed separately in the vicinity of the solid electrolyte element.

A device of a second aspect of the invention for measuring combustible-gas concentration is characterized in that the detection electrode comprises a first electrode layer formed on the surface of the solid electrolyte element and a second electrode layer formed on the surface of the first electrode layer; the first electrode layer containing at least one of platinum and gold; and the second electrode layer containing at least one of gold and a metallic oxide (except for a case where the first electrode layer is identical in composition with the second electrode layer).

The above-mentioned "combustible gas," "reference electrode," "detection electrode," "heater element," "solid electrolyte element," and "metallic oxide" are similar to those of the first aspect of the invention. By employing the detection electrode structure comprising the "first electrode layer" and the "second electrode layer," sensor output can be reduced (or rather lowered) for a gas to be measured which does not contain a combustible gas (hereinafter, this sensor output is called merely "offset"). Also, adhesion of the detection electrode to the solid electrolyte element can be improved in this structure.

The offset is apt to increase when an electrode contains a metallic oxide is formed in direct contact with the solid electrolyte element. An increase in the offset is not preferred, since the sensor output relatively decreases for a combustible gas contained in the gas to be measured. By contrast according to the invention, by forming the first electrode layer containing at least one of platinum and gold, between the solid electrolyte element and the second electrode layer that contains a metallic oxide, the offset can be suppressed to a low level such that a combustible gas can be detected and measured more accurately.

By employing a detection electrode contains gold and a metallic oxide, a device for measuring combustible-gas concentration can suppress offset to 0–40 mV and further to 0–10 mV. The device for measuring combustible-gas concentration equipped with the detection electrode which contains gold and a metallic oxide is 40–120 mV lower in offset than one equipped with a detection electrode which contains only gold.

When an electrode contains a metallic oxide is formed in contact with the solid electrolyte element, adhesion between the solid electrolyte element and the detection electrode may become insufficient. By contrast, by forming the first electrode layer, which contains at least one of platinum and gold, between the solid electrolyte element and the second electrode layer, which contains a metallic oxide, adhesion between the solid electrolyte element and the detection electrode can be greatly improved.

In order to further improve the adhesion, a thin layer (thickness: 0.01–30 $\mu$m) of plated gold or a thin layer (thickness: 0.01–30 $\mu$m) of a baked organic gold compound may be formed between the first electrode layer and the second electrode layer. Also, by forming a similar thin layer between the solid electrolyte element and the first electrode layer, an adhesive layer can be improved.

When the amount of the first electrode layer is taken as 100 parts by weight (hereinafter, "parts"), the first electrode layer preferably contains platinum or gold in an amount of not less than 50 parts, more preferably not less than 80 parts, further preferably not less than 90 parts. The first electrode layer may be formed from only platinum or gold. The first electrode layer may contain rhodium or indium in addition to platinum or gold. These elements improve heat resistance of the first electrode layer. For example, the first electrode layer may contain 90 parts of platinum and 10 parts of rhodium.

The thickness of the first electrode layer is not particularly limited, but is preferably not greater than 25 $\mu$m, more preferably not greater than 5 $\mu$m.

A device of a third aspect of the invention for measuring combustible-gas concentration is characterized in that the detection electrode comprises a first electrode layer formed on the surface of the solid electrolyte element, a second electrode layer formed on the surface of the first electrode layer, and a third electrode layer formed on the surface of the second electrode; the first electrode layer containing a predominant amount of platinum; the second electrode layer containing a predominant amount of gold; and the third electrode layer containing a metallic oxide and optionally gold.

The above-mentioned "combustible gas," "reference electrode," "detection electrode," "heater element," "solid electrolyte element," and "metallic oxide" are similar to those of the first aspect of the invention. When the amount of the above-mentioned "first electrode layer" is taken as 100 parts, the first electrode layer preferably contains platinum in an amount of not less than 80 parts (more preferably not less than 90 parts, further preferably not less than 95 parts). When the amount of the above-mentioned "second electrode layer" is taken as 100 parts, the second electrode layer preferably contains gold in an amount of not less than 80 parts (more preferably not less than 90 parts, further preferably not less than 95 parts).

By employing the detection electrode comprising the "first electrode layer," the "second electrode layer," and the "third electrode layer," offset can be reduced as in the case of the second aspect of the invention. Also, adhesion between the detection electrode and the solid electrolyte element can be further improved. As in the case of the second aspect of the invention, a thin layer of plated gold or a thin layer of a baked organic gold compound may be formed between the electrodes so as to improve adhesion between the detection electrode and the solid electrolyte element.

The detection electrode in the first through third aspects of the invention may be formed on the entire portion of the surface of the solid electrolyte element which is exposed to a gas to be measured. However, preferably, as specified in a fourth aspect of the invention, the detection electrode is formed on the surface of the solid electrolyte element at only a portion corresponding to a heating resistor formed within the heater element (hereinafter, this portion is called a "uniformly heated high-temperature portion"). The "uniformly heated high-temperature portion" is a portion of the surface of the solid electrolyte element under which the heating resistor is present.

Preferably, as specified in a fifth aspect of the invention, the detection electrode is formed on the surface of the solid electrolyte element at only a portion extending from an end portion of the solid electrolyte element to the vicinity of the interface between a heating resistor and a heating-resistor lead portion, which are formed within the heater element (hereinafter, this portion is also called a "uniformly heated high-temperature portion").

When the device for measuring combustible-gas concentration comprises a solid electrolyte element having the form of a closed-bottomed cylinder, the portion extending between the "interface between a heating resistor and a heating-resistor lead portion" and the "end portion of the solid electrolyte element" is a portion enclosed by B and T shown in FIGS. 5 and 6. When the device for measuring combustible-gas concentration comprises a solid electrolyte element of a laminate form, the portion extending between the "interface between a heating resistor and a heating-resistor lead portion" and the "end portion of the solid electrolyte element" is a portion enclosed by B and T shown in FIG. 7.

The uniformly heated high-temperature portion in the fourth and fifth aspects of the invention is where the surface temperature of the solid electrolyte element can easily be maintained at higher temperature in a uniform, stable manner by means of the heater element. Accordingly, by forming the electrodes on only this uniformly heated high-temperature portion, temperature dependence of sensor output can be suppressed to a low level. The surface temperature of the solid electrolyte element as measured at this uniformly heated high-temperature portion is maintained preferably at 350–750° C. (more preferably 450–650° C., further preferably 500–600° C.). Further, the surface temperature of the uniformly heated high-temperature portion can be controlled preferably to a set temperature ±50° C. (more preferably a set temperature +30° C., further preferably a set temperature ±10° C.).

In the case of a solid electrolyte element having the form of a closed-bottomed cylinder, for example, when the interface between the heating resistor and the heating-resistor lead portion is represented by B shown in FIGS. 5 and 6, this uniformly heated high-temperature portion is a portion enclosed by a plane which is located in parallel with the interface within a 5 mm range (preferably within a 2 mm range) with respect to the interface, and plane T which is in parallel with the interface and includes an end portion of the solid electrolyte element.

In the case of a solid electrolyte element of a laminate form, when the interface between the heating resistor and the heating-resistor lead portion is represented by B shown in FIG. 7, this uniformly heated high-temperature portion is a portion enclosed by a plane which is located in parallel with the interface within a 3 mm range (preferably within a 1 mm range) with respect to the interface, and a plane which is in parallel with the interface and includes an end portion of the solid electrolyte element. Notably, the detection element may be formed on the entire surface of the uniformly heated high-temperature portion or on a portion of the surface of the uniformly heated high-temperature portion. Preferably, the reference electrode is formed on or in a portion of the uniformly heated high-temperature portion.

A device of a sixth aspect of the invention for measuring combustible-gas concentration is characterized in that the detection electrode contains gold and optionally platinum and is formed on the solid electrolyte element at only a portion extending from an end portion of the solid electrolyte element to the vicinity of the interface between a heating resistor and a heating-resistor lead portion, which are formed within the heater element.

The above-mentioned "combustible gas," "reference electrode," "detection electrode," "heater element," "solid electrolyte element," and "metallic oxide" are similar to those of the first aspect of the invention. The above-mentioned "vicinity of the interface between a heating resistor and a heating-resistor lead portion" and "end portion of the solid electrolyte element" are similar to those of the fourth aspect of the invention.

In the devices of the first through sixth aspects of the invention for measuring combustible-gas concentration, when the first electrode layer contains platinum (preferably not less than 50 parts, more preferably not less than 80 parts) and the second electrode layer contains gold, it is preferable that the second electrode layer be formed from paste which contains gold powder of an average grain size of 0.1–100 µm (preferably 0.2–50 µm, more preferably 0.5–30 µm), by baking the paste. When the average grain size of gold powder is less than 0.1 µm, sufficient sensitivity is not obtained. When the average grain size is in excess of 100 µm, the second electrode layer fails to have a uniform thickness, potentially causing variations in sensor output.

A device of a seventh aspect of the invention for measuring combustible-gas concentration is characterized in that the detection electrode comprises a first electrode layer formed on the surface of the solid electrolyte element and a second electrode layer formed on the surface of the first electrode layer; the first electrode layer containing platinum; the second electrode layer containing gold (except for a case where the first electrode layer is identical in composition with the second electrode layer); and the second electrode layer is formed from paste containing gold powder of an average grain size of 1–100 µm (preferably 2–50 µm, more preferably 5–30 µm) and by baking the paste.

The above-mentioned "combustible gas," "reference electrode," "detection electrode," "heater element," and "solid electrolyte element" are similar to those of the first aspect of the invention. When the average grain size of gold powder is less than 1 µm, sufficient improvement in sensitivity is not attained. When the average grain size is in excess of 100 µm, the second electrode layer fails to have a uniform thickness, potentially causing variations in sensor output. By forming the detection electrode from gold powder of such a large grain size, sensitivity can be improved in detecting a combustible gas. The specific reason why sensitivity is improved is not definitely known. Gold powder of a large grain size tends to maintain a large grain size even after being subjected to baking. It is considered that gold contained in the detection electrode is preferably present while maintaining a large grain size even after baking.

As in the case of the first aspect of the invention, the second electrode layer may contain a metallic oxide in addition to gold. When the second electrode layer contains a predominant amount of gold and a third electrode layer is formed on the surface of the second electrode layer, the third electrode layer may contain gold and a metallic oxide. Further, when the first electrode layer contains gold and the third electrode layer contains gold, it is preferable that the first and third electrode layers be formed from respective pastes which contain gold powder of similar grain sizes.

Preferably, as specified in an eighth aspect of the invention, a diffusion layer is formed on the surface of the detection electrode in any of the first through seventh aspects of the invention. The above-mentioned "diffusion layer" is not particularly limited so long as it permits a combustible gas contained in a gas to be measured to reach the detection electrode. The diffusion layer is conventionally formed from spinel and/or alumina. Passing through this diffusion layer, a gas to be measured reaches the detection electrode at a substantially constant velocity or flow rate, regardless of velocity or flow rate at which the gas to be measured reaches the surface of the diffusion layer. That is, dependence on velocity or flow rate of a gas to be measured can be reduced. The diffusion layer may also serve as a protection layer against poisoning and a reinforcement layer for increasing strength. The diffusion layer may be formed of two or more layers.

Preferably, as specified in a ninth aspect of the invention, the diffusion layer contains a component which oxidizes at least one of hydrogen and carbon monoxide. The device of the present aspect of the invention for measuring combustible-gas concentration may be particularly sensitive to hydrogen and in some cases carbon monoxide among combustible gases and may provide sensor output accordingly. In order to obtain sensor output which excludes a detection signal associated with at least one of hydrogen and carbon monoxide, hydrogen and/or carbon monoxide is oxidized or adsorbed so as to prevent the same from reaching the detection electrode. Thus, combustible gases excluding hydrogen and/or carbon monoxide can be accurately detected and measured. Examples of a catalytic component for oxidizing hydrogen include Pb, Ag, Au, Pd, Pt, Ir, Ru, Rh, Co, Ni, Mn, Cu, Cd, Fe, V, Cr, Ce, Y and La. In order to obtain sensor output which excludes a detection signal associated with carbon monoxide, the diffusion layer may contain a component capable of selectively or preferentially oxidizing or adsorbing carbon monoxide. Examples of such a component include Pb, Ag, Au, Pd, Pt, Ir, Ru, Rh, Co, Ni, Mn, Cu, Cd, Fe, V, Cr, Ce, Y and La. Notably, these components contained in the diffusion layer oxidize nitrogen monoxide and reduce other nitrogen oxides.

Particularly preferably, as specified in a tenth aspect of the invention, the diffusion layer contains at least one of platinum and palladium. When the diffusion layer contains "platinum," sensor output for hydrogen and particularly carbon monoxide can be reduced as compared with the case where the diffusion layer does not contain platinum. In this case, sensor output for combustible gases other than carbon monoxide also decreases. However, since sensor output for hydrogen and carbon monoxide—which would otherwise be detected with particular sensitivity—is decreased, sensitivity for combustible gases other than hydrogen and carbon monoxide relatively increases. Thus, even when a gas to be measured contains hydrogen and carbon monoxide, their effect on measurement can be suppressed to a small degree, whereby combustible gases other than hydrogen and carbon monoxide can be accurately detected and measured.

When the device for measuring combustible-gas concentration in which the diffusion layer contains platinum is applied to measurement of a gas to be measured which contains hydrogen; specifically, a gas to be measured which contains $H_2$ (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes 570° C., sensor output for hydrogen can be reduced by 80 mV or more (approx. 25% or more) as compared with measurement by a device in which the diffusion layer does not contain platinum.

When the device for measuring combustible-gas concentration in which the diffusion layer contains platinum is applied to measurement of a gas to be measured which contains carbon monoxide; specifically, a gas to be measured which contains CO (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes 570° C., sensor output for carbon monoxide can be reduced by 80 mV or more (approx. 80% or more), further by 85 mV or more (approx. 85% or more), as compared with measurement by a device in which the diffusion layer does not contain platinum.

When the diffusion layer contains "palladium," sensor output for combustible gases other than carbon monoxide can be increased as compared with the case where the diffusion layer does not contain palladium. At the same time, sensitivity for carbon monoxide can be reduced. Accordingly, while the effect of carbon monoxide—which would otherwise be detected with particular sensitivity—on measurement is suppressed to a small degree, combustible gases other than carbon monoxide can be accurately detected and measured.

When the device for measuring combustible-gas concentration in which the diffusion layer contains palladium is applied to measurement of a gas to be measured which contains carbon monoxide; specifically, a gas to be measured which contains propylene (1000 ppm) or CO (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes 570° C., sensor output for carbon monoxide can be reduced by 14 mV or more (approx. 15% or more), further by 20 mV or more (approx. 20% or more), as compared with measurement by a device in which the diffusion layer does not contain palladium. Further, this device for measuring combustible-gas concentration can improve sensor output for propylene by 15 mV or more (approx. 13% or more), further by 20 mV or more (approx. 16% or more).

Preferably, as specified in an eleventh aspect of the invention, the device of the present invention for measuring combustible-gas concentration further comprises temperature control means for controlling voltage applied to the heater element on the basis of the internal resistance of the solid electrolyte element. The structure of the above-mentioned "temperature control means" is not particularly limited. Typically, the temperature control means comprises means for measuring the internal resistance of the solid electrolyte element and applied-voltage control means for controlling voltage applied to the heater element on the basis of the internal resistance. This internal resistance can be obtained by measuring resistance between the reference electrode and the detection electrode, which are formed on the solid electrolyte element. Alternatively, another conductive layer serving as an internal-resistance detection electrode may be formed on the solid electrolyte element, and the resistance between the conductive layer and the detection electrode or between the conductive layer and the reference electrode may be measured. The internal-resistance detection electrode may be formed separately from the reference electrode and the detection electrode (for example, as shown in FIGS. 6 and 9).

Preferably, as specified in a twelfth aspect of the invention, the solid electrolyte element assumes the form of a closed-bottomed cylinder; the heater element disposed within the solid electrolyte element assumes a rod form; the central axis of the solid electrolyte element and the central axis of the heater element substantially coincide with each other; and at least a portion of an end of the heater element is in contact with the inner surface of a bottom portion of the solid electrolyte element.

The above-mentioned "substantially coincide with each other" means that the solid electrolyte element and the heater element are coaxial or that the central axes are separated from each other by not more than 500 $\mu$m (preferably, not more than 200 $\mu$m, more preferably 50 $\mu$m).

The above disposition of the heater element expands a portion of the surface of the solid electrolyte element which is maintained at high temperature (preferably, 400–650° C., more preferably 450–600° C., further preferably 480–590° C.). Further, the high-temperature portion of small temperature variations can be expanded (where the difference between the maximum and minimum temperatures falls within 100° C., more preferably within 80° C., further preferably within 50° C.). That is, even when the detection electrode is formed, the temperature dependence of the device for measuring combustible-gas concentration derived from temperature variations on the surface of the solid electrolyte element can be reduced.

In this portion of the surface of the solid electrolyte element of high temperature and uniform temperature distribution (not necessarily identical with the uniformly heated high-temperature portion), when the device for measuring combustible-gas concentration has a maximum surface temperature of 400–650° C., the difference between average temperature as measured on the surface of the device at a position 1 mm from a bottom portion of the device toward a head portion of the device and average temperature as measured on the surface of the device at a position 5 mm from the bottom portion toward the head portion can be not greater than 50° C. (preferably not greater than 40° C., more preferably not greater than 30° C.). When the device for measuring combustible-gas concentration has a maximum surface temperature of 400–650° C., variations in maximum temperature as measured at four locations which are 90 degrees apart from each other around the device can be suppressed to not greater than 60° C. (preferably not greater than 50° C., further preferably 40° C.).

The surface of the device for measuring combustible-gas concentration means such a surface as observed after removal of a mounting shell of metal. Specifically, the surface temperature of the device is the temperature of the surface of the diffusion layer when a diffusion layer is formed, or the temperature of the surface of the detection electrode or the solid electrolyte element when a diffusion layer is not formed.

For the devices of the first through eleventh aspects of the invention for measuring combustible-gas concentration, reducing dependence of sensor output on temperature is important. To this end, preferably, the detection electrode is formed at only the uniformly heated high-temperature portion. Further, temperature distribution in the uniformly heated high-temperature portion is preferably uniform. Accordingly, preferably, as specified in the twelfth aspect of the invention, the central axis of the solid electrolyte element and the central axis of the heater element coincide or substantially coincide with each other. This feature establishes uniform temperature distribution on the surface of the uniformly heated high-temperature portion of the device for measuring combustible-gas concentration.

Further, at least a portion of the end of the heater element is in contact with the inner surface of a bottom portion of the solid electrolyte element, thereby expanding uniform temperature distribution up to the end of the bottom portion of the device for measuring combustible-gas concentration. In order to attain such contact, an end portion of the heater element may be formed such that the diameter decreases toward the end of the heater element. For example, the end portion of the heater element may be rounded as is the inner surface of the bottom portion of the solid electrolyte element.

In the devices of the first through twelfth aspects of the invention for measuring combustible-gas concentration, as a result of the detection electrode assuming the above-described structure, offset can be reduced. However, oxygen concentration influences measurement by the device of the present invention for measuring combustible-gas concentration. Thus, preferably, in order to accurately detect and measure a combustible gas, sensor output is corrected for oxygen concentration through subtraction of sensor output for oxygen concentration.

Such correction may be performed by, for example, the following methods: a portion of the solid electrolyte element of the device for measuring combustible-gas concentration is used as an oxygen sensor for measuring oxygen concentration; an oxygen sensor for measuring oxygen concentration is disposed separately from the device for measuring combustible-gas concentration; and a reference electrode and a detection electrode are formed so as to be exposed to the same gas to be measured, thereby directly obtaining sensor output after sensor output for oxygen concentration is cancelled.

A device of a thirteenth aspect of the invention for measuring hydrocarbon-gas concentration comprises an oxygen-ion-conductive solid electrolyte element, a reference electrode and a detection electrode formed on the surface of the solid electrolyte element, and a heater element for heating the solid electrolyte element. The device is characterized in that the detection electrode contains gold and a metallic oxide.

Examples of the above-mentioned "hydrocarbon gas" include hydrocarbons having 2–15 carbon atoms. The device of the present aspect of the invention for measuring hydrocarbon-gas concentration can sensitively detect hydrocarbons, particularly unsaturated hydrocarbons having 2–15 carbon atoms, and can accurately measure the concentration thereof. The above-mentioned "reference electrode" is an electrode which is brought into contact with a reference gas or is placed in an oxygen atmosphere of constant pressure established by means of an oxygen pump, and/or which can indicate a lower electric potential than does the detection electrode, upon contact with a hydrocarbon gas component contained in a gas being measured. The "detection electrode," "heater element," "solid electrolyte element," and "metallic oxide" are similar to those of the first aspect of the invention.

A device of a fourteenth aspect of the invention for measuring hydrocarbon-gas concentration is characterized in that the detection electrode comprises a first electrode layer formed on the surface of the solid electrolyte element and a second electrode layer formed on the surface of the first electrode layer; the first electrode layer containing at least one of platinum and gold; and the second electrode layer containing at least one of gold and a metallic oxide (except for a case where the first electrode layer is identical in composition with the second electrode layer).

A device of a fifteenth aspect of the invention for measuring hydrocarbon-gas concentration is characterized in that the detection electrode comprises a first electrode layer formed on the surface of the solid electrolyte element, a second electrode layer formed on the surface of the first electrode layer, and a third electrode layer formed on the surface of the second electrode; the first electrode layer containing a predominant amount of platinum; the second electrode layer containing a predominant amount of gold; and the third electrode layer containing a metallic oxide and optionally gold.

In the fourteenth and fifteenth aspects of the invention, "hydrocarbon gas," "reference electrode," "detection electrode," "heater element," "solid electrolyte element," and "metallic oxide" are similar to those of the thirteenth aspect of the invention. In the fourteenth aspect of the invention, "first electrode layer" and "second electrode layer" are similar to those of the second aspect of the invention. In the fifteenth aspect of the invention, "first electrode layer" and "second electrode layer" are similar to those of the third aspect of the invention.

Preferably, as specified in a sixteenth aspect of the invention and a seventeenth aspect of the invention, as in the case of the fourth and fifth aspects of the invention, the detection electrode is formed at only a uniformly heated high-temperature portion.

A device of an eighteenth aspect of the invention for measuring hydrocarbon-gas concentration is characterized in that the detection electrode contains gold and optionally platinum and is formed on the solid electrolyte element at only a portion extending from an end portion of the solid electrolyte element to the vicinity of the interface between a heating resistor and a heating-resistor lead portion, which are formed within the heater element.

The above-mentioned "hydrocarbon gas," "reference electrode," "detection electrode," "heater element," and "solid electrolyte element" are similar to those of the thirteenth aspect of the invention. The above-mentioned "vicinity of the interface between a heating resistor and a heating-resistor lead portion" and "end portion of the solid electrolyte element" are similar to those of the sixteenth aspect of the invention.

A device of a nineteenth aspect of the invention for measuring hydrocarbon-gas concentration is characterized in that the detection electrode comprises a first electrode layer formed on the surface of the solid electrolyte element and a second electrode layer formed on the surface of the first electrode layer; the first electrode layer containing platinum; the second electrode layer containing gold (except for a case where the first electrode layer is identical in composition with the second electrode layer); and the second electrode layer is formed from paste containing gold powder of an average grain size of 1–100 $\mu$m (preferably 2–50 $\mu$m, more preferably 5–30 $\mu$m) and by baking the paste.

The above-mentioned "hydrocarbon gas," "reference electrode," "detection electrode," "heater element," and "solid electrolyte element" are similar to those of the thirteenth aspect of the invention. The average grain size of gold power is similar to that associated with the seventh aspect of the invention.

Preferably, as specified in a twentieth aspect of the invention, as in the case of the eighth aspect of the invention, a diffusion layer is formed on the surface of the detection electrode in any of the thirteenth through nineteenth aspects of the invention. Preferably, as specified in a twenty-first aspect of the invention, as in the case of the ninth aspect of the invention, the diffusion layer contains a component which oxidizes at least one of hydrogen and carbon monoxide. Particularly, as specified in a twenty-second aspect of the invention, as in the case of the tenth aspect of the invention, the diffusion layer contains at least one of platinum and palladium.

When the device for measuring hydrocarbon-gas concentration in which the diffusion layer contains platinum is applied to measurement of a gas to be measured which contains hydrogen; specifically, a gas to be measured which contains $H_2$ (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes 570° C., sensor output for hydrogen can be reduced by 80 mV or more (approx. 25% or more) as compared with measurement by a device in which the diffusion layer does not contain platinum.

When the device for measuring hydrocarbon-gas concentration in which the diffusion layer contains platinum is applied to measurement of a gas to be measured which contains carbon monoxide; specifically, a gas to be measured which contains CO (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes 570° C., sensor output for carbon monoxide can be reduced by 80 mV or more (approx. 80% or more), further by 85 mV or more (approx. 85% or more), as compared with measurement by a device in which the diffusion layer does not contain platinum.

When the device for measuring hydrocarbon-gas concentration in which the diffusion layer contains palladium is applied to measurement of a gas to be measured which contains carbon monoxide; specifically, a gas to be measured which contains propylene (1000 ppmC) or CO (1000 ppm), $O_2$ (7%), $CO_2$ (10%), $H_2O$ (10%), and $N_2$ (balance) and which has a temperature of 300° C. and flows at 15 liters/min, and the device is controlled in the course of measurement such that the surface temperature of the detection electrode becomes approximately 570° C., sensor output for carbon monoxide can be reduced by 14 mV or more (approx. 15% or more), further by 20 mV or more (approx. 20% or more), as compared with measurement by a device in which the diffusion layer does not contain palladium. Further, this device for measuring hydrocarbon-gas concentration can improve sensor output for propylene by 15 mV or more (approx. 13% or more), further by 20 mV or more (approx. 16% or more).

Preferably, as specified in a twenty-third aspect of the invention, as in the case of the eleventh aspect of the invention, the device of the present invention for measuring hydrocarbon-gas concentration further comprises temperature control means for controlling voltage applied to the heater element on the basis of the internal resistance of the solid electrolyte element. Preferably, as specified in a twenty-fourth aspect of the invention, as in the case of the twelfth aspect of the invention, the solid electrolyte element assumes the form of a closed-bottomed cylinder; the heater element disposed within the solid electrolyte element assumes a rod form; the central axis of the solid electrolyte element and the central axis of the heater element substantially coincide with each other; and at least a portion of an end of the heater element is in contact with the inner surface of a bottom portion of the solid electrolyte element. Preferably, in the devices of the thirteenth through twenty-fourth aspects of the invention for measuring hydrocarbon-gas concentration, as in the case of the previously-described devices for measuring combustible-gas concentration, sensor output is corrected for oxygen concentration through subtraction of sensor output for oxygen concentration.

The invention also provides, as twenty-fifth and twenty-sixth aspects, methods for measuring combustible-gas concentration or for measuring hydrocarbon-gas concentration, using a device according to one of the first through twelfth aspects of the invention or thirteenth through twenty-fourth aspects of the invention, respectively, wherein the internal resistance of the solid electrolyte is measured periodically, and a voltage applied to the heater element is controlled such that the internal resistance becomes constant.

Note that throughout this specification, the terms "propene" and "propylene" are used synonymously. Propene is the more strictly correct term, whereas propylene is the term commonly used in this field.

Figure 1:
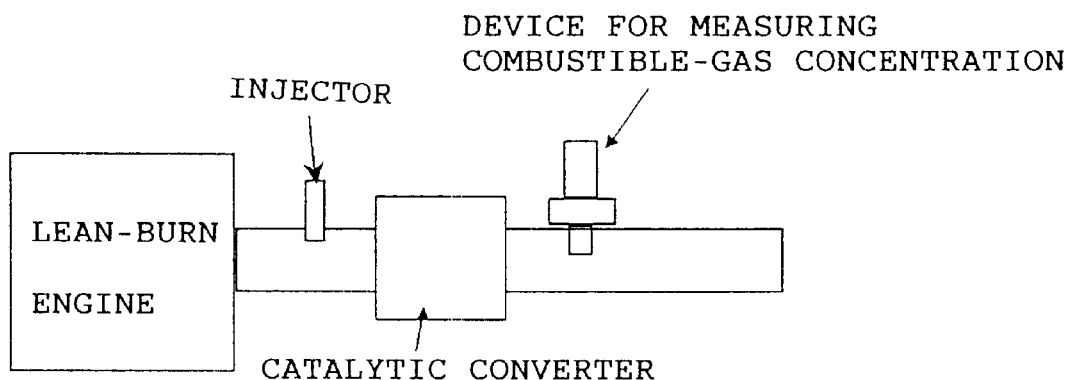
FIG. 1 is a diagram showing an example of an application of a device for measuring combustible-gas concentration or a device for measuring hydrocarbon-gas concentration.
Figure 2:
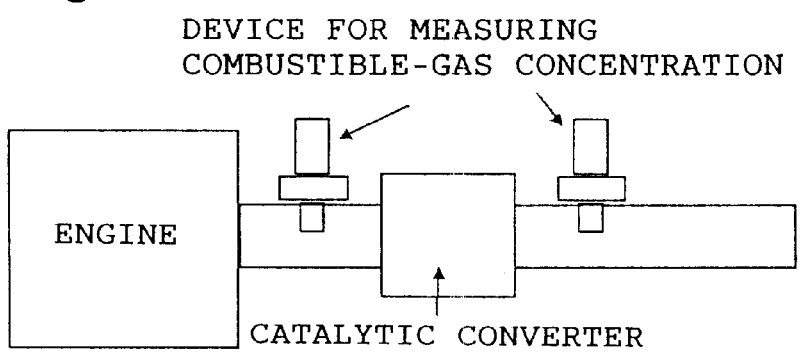
FIG. 2 is a diagram showing an example of an application of a device for measuring combustible-gas concentration or a device for measuring hydrocarbon-gas concentration.
Figure 3:
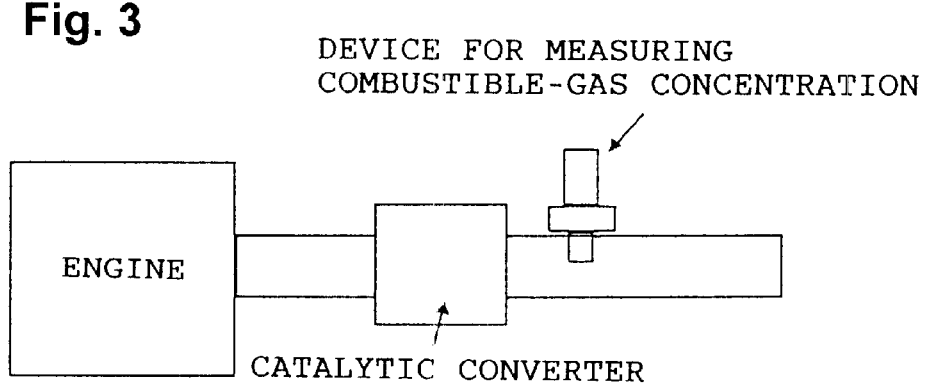
FIG. 3 is a diagram showing an example of an application of a device for measuring combustible-gas concentration or a device for measuring hydrocarbon-gas concentration.
Figure 4:
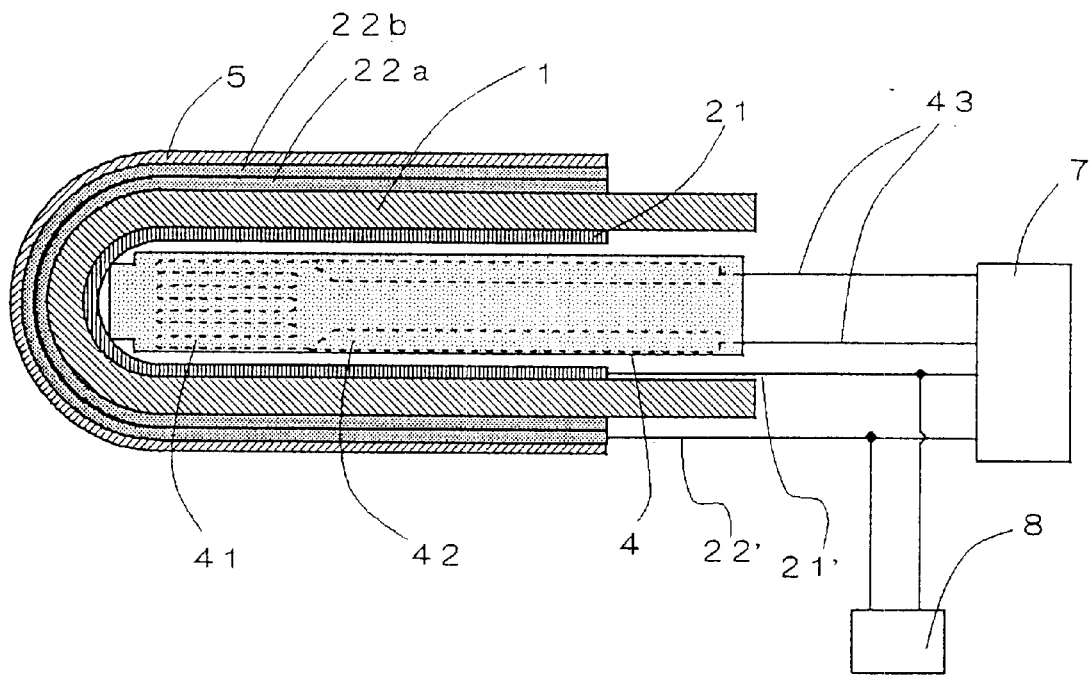
FIG. 4 is a schematic longitudinal sectional view of a device for measuring combustible-gas concentration or a device for measuring hydrocarbon-gas concentration, which device is equipped with a closed-bottomed solid electrolyte element.
Figure 5:
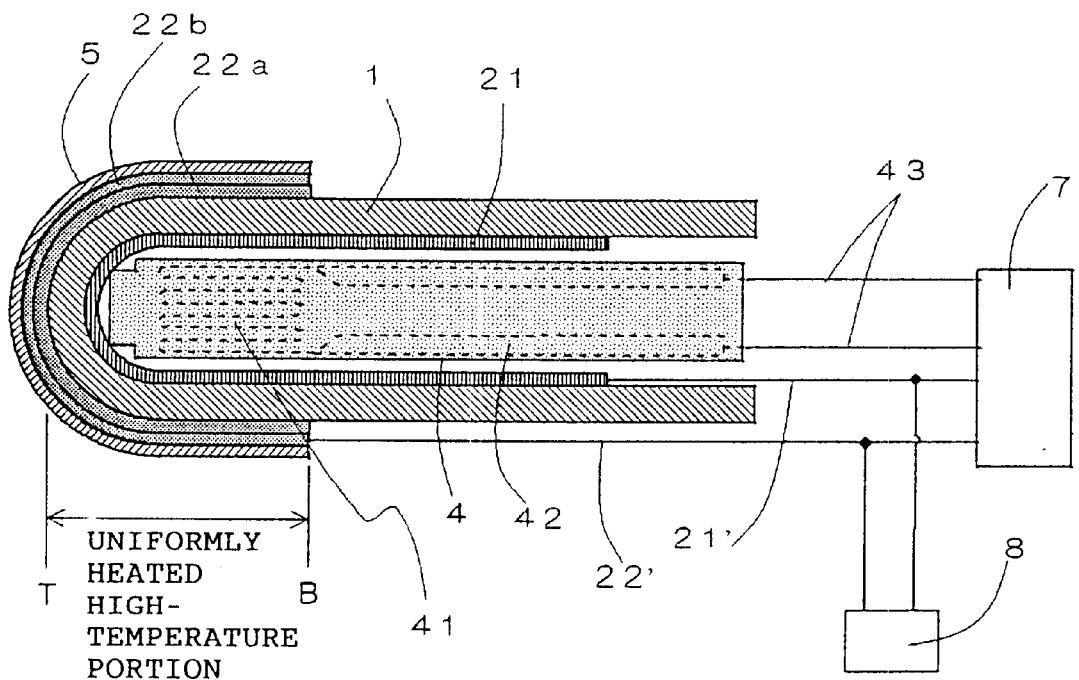
FIG. 5 is a schematic longitudinal sectional view of a device for measuring combustible-gas concentration or a device for measuring hydrocarbon-gas concentration, which device is equipped with a closed-bottomed solid electrolyte element.
Figure 6:
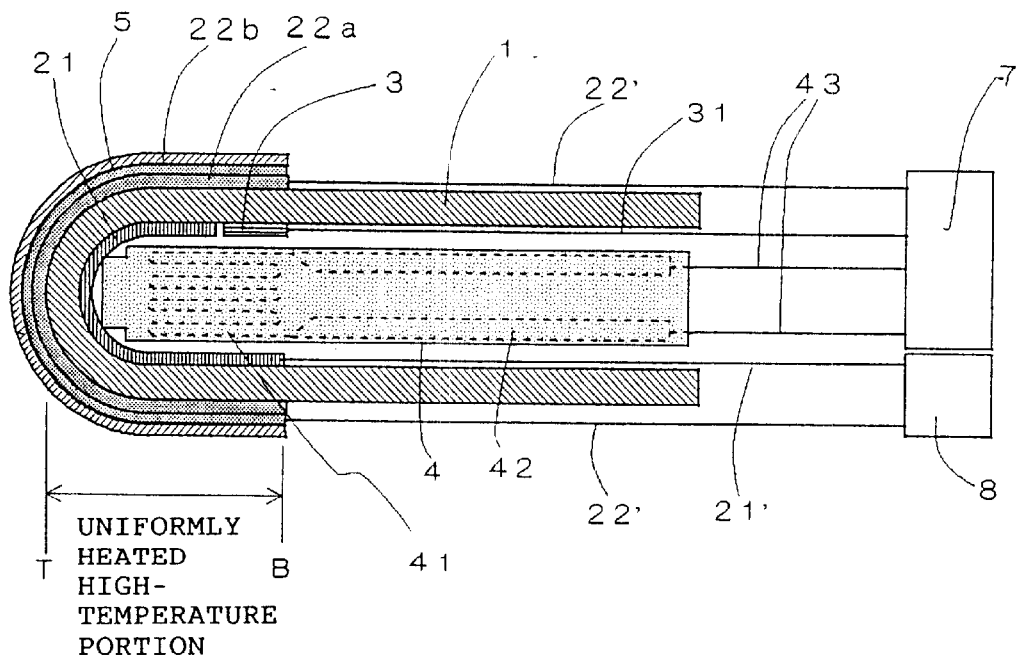
FIG. 6 is a schematic longitudinal sectional view of a device of the present invention for measuring combustible-gas concentration or a device of the present invention for measuring hydrocarbon-gas concentration, which device is equipped with a closed-bottomed solid electrolyte element.
Figure 7:
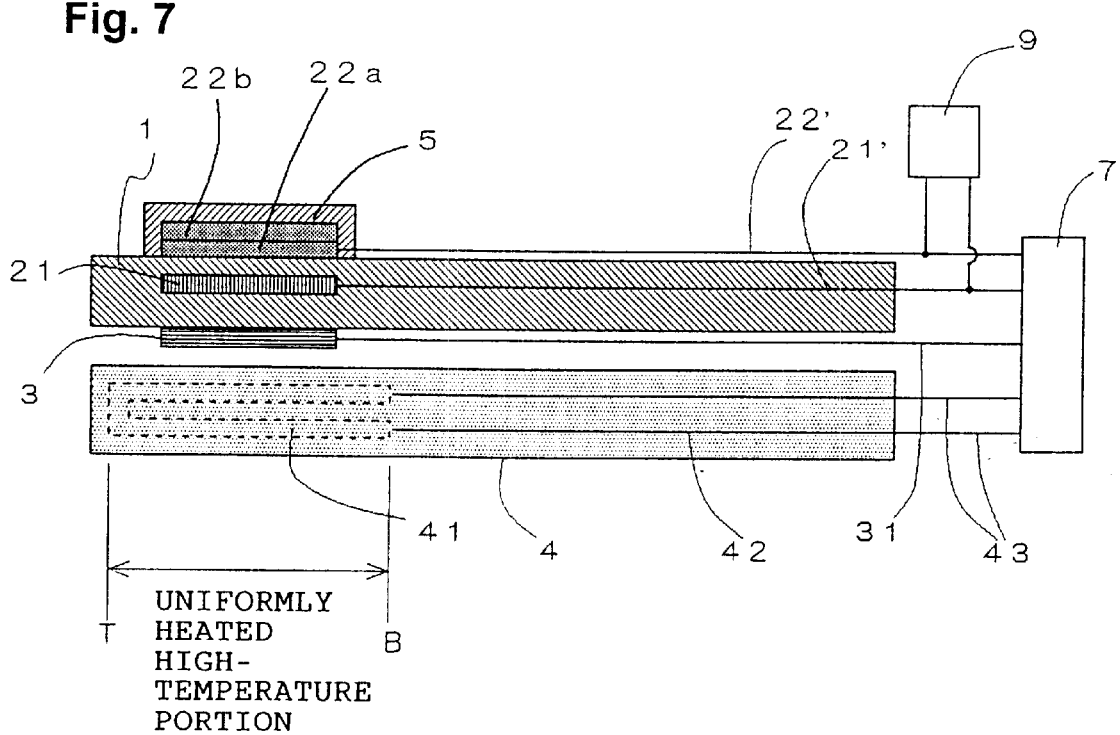
FIG. 7 is a schematic transverse sectional view of a laminate-type device for measuring combustible-gas concentration or a laminate-type device for measuring hydrocarbon-gas concentration.
Figure 8:
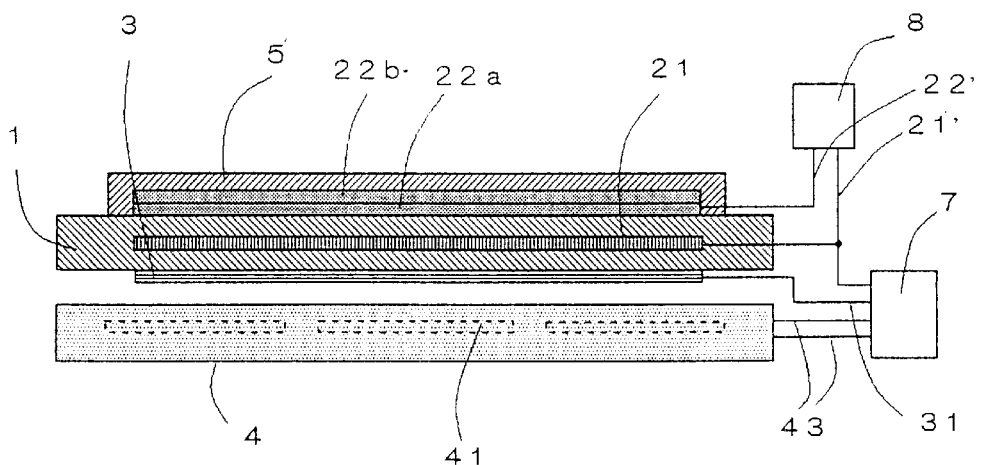
FIG. 8 is a schematic transverse sectional view of a laminate-type device for measuring combustible-gas concentration or a laminate-type device for measuring hydrocarbon-gas concentration.
Figure 9:
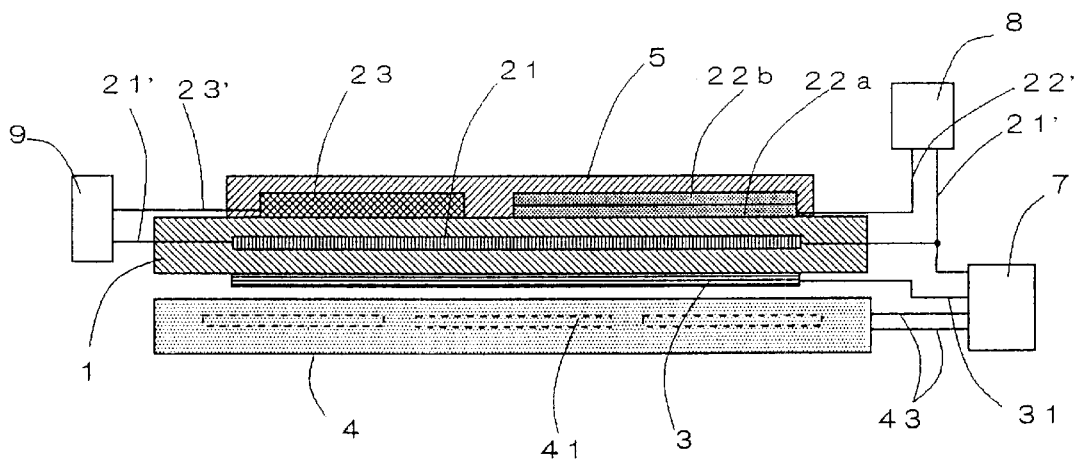
FIG. 9 is a schematic transverse sectional view of a device for measuring combustible-gas concentration or a device for measuring hydrocarbon-gas concentration, which device is equipped with oxygen concentration measurement means for making correction for oxygen concentration.
Figure 10:
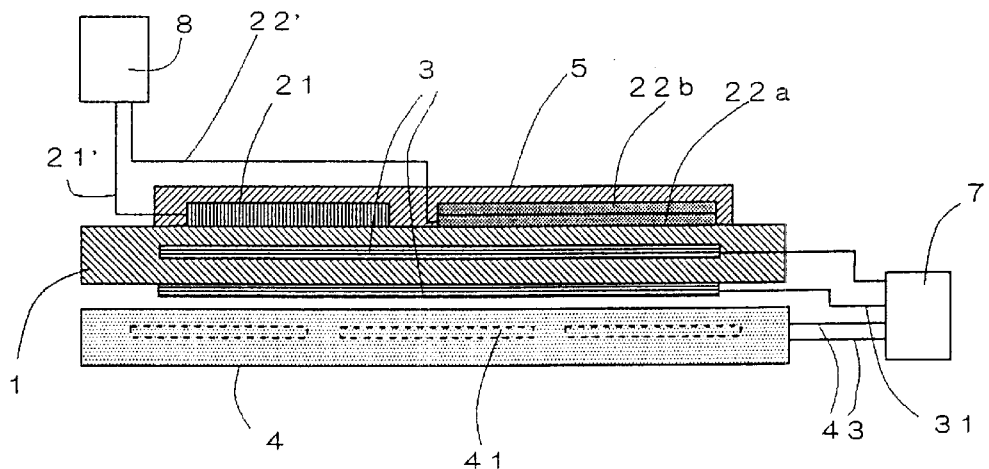
FIG. 10 is a schematic transverse sectional view of a laminate-type device for measuring combustible-gas concentration or a laminate-type device for measuring hydrocarbon-gas concentration.

Reference Numerals are used to identify items shown in the drawings as follows:
1: solid electrolyte element
21: reference electrode
21': reference electrode lead wire
22a: first electrode layer
22b: second electrode layer
22': detection electrode lead wire
23: oxygen detection electrode
23': oxygen detection electrode lead wire
3: internal-resistance measurement electrode
31: internal-resistance measurement lead wire
4: heater element
41: heating resistor
42: heating-resistor lead portion
43: heater element lead wires
5: diffusion layer
6: reinforcement layer
7: temperature controller
8: sensor output measurement means
9: correction-for-oxygen-concentration means
B: interface between the heating resistor and the heating-resistor lead portion
T: plane including the end portion of the solid electrolyte element

DESCRIPTION OF THE PREFERRED EMBODIMENTS

Embodiments of the present invention will next be described in detail by way of example. However, the present invention should not be construed as being limited thereto.

[1] Manufacture of Closed-Bottomed Cylindrical Devices for Measuring Combustible-Gas Concentration Yttria stabilized zirconia (hereinafter called merely YSZ) powder which contains 4.5 mol % $Y_2O_3$ was filled into a rubber die, followed by compacting. A detection electrode lead wire pattern was printed on the surface of each of the obtained green compacts using paste. Then, the green compacts were fired, thereby yielding closed-bottomed cylindrical solid electrolyte elements. The inner surface of each of the solid electrolyte elements was plated with platinum to thereby form a layer serving as a reference electrode. Next, a layer serving as a first electrode layer was formed by platinum-plating. Gold powder (90 parts) and metallic-oxide powder (10 parts) were mixed. To the resultant powder mixture, a binder, a dispersant, and butyl carbitol as solvent were added in respectively predetermined amounts. The obtained mixture was kneaded into paste. The paste was applied onto the platinum plating layer to thereby form a layer serving as a second electrode layer. The thus-prepared solid electrolyte elements were subjected to baking at a temperature of 880° C. for 10 minutes. Subsequently, a diffusion layer which contained spinel was formed by thermal spraying on the surface of the detection layer of each of the solid electrolyte elements. A heater element was disposed in each of the solid electrolyte elements such that an end portion abutted an inner bottom portion of the solid electrolyte element. Next, a reference electrode lead wire, a detection electrode lead wire, and heater element lead wires of each of the resultant solid electrolyte elements were connected to a temperature controller. Devices for measuring combustible-gas concentration were thus obtained.

[2] Evaluation of Detection Electrodes (1) Comparison of Temperature Dependence of Offset Devices 1, 2 and 3 were used for measuring combustible-gas concentration which had been manufactured according to the method described in [1] and in the following manner: device 1: the detection electrode contains only gold; device 2: the detection electrode is formed of a single layer which contains gold and a metallic oxide; and device 3: the detection electrode is formed of two layer—the first electrode layer formed through platinum-plating and the second electrode layer which contains 90 parts of gold and 10 parts of indium oxide. Temperature dependence of offset was compared among the devices 1, 2 and 3. Measurement was carried out at room temperature in the atmosphere. While the heater element was electrically energized such that the internal resistance of the solid electrolyte element became 500Ω, 1000Ω, 1500Ω and 2000Ω, offset and temperature within the solid electrolyte element were measured. The results are shown in FIG. 11.

Figure 11:
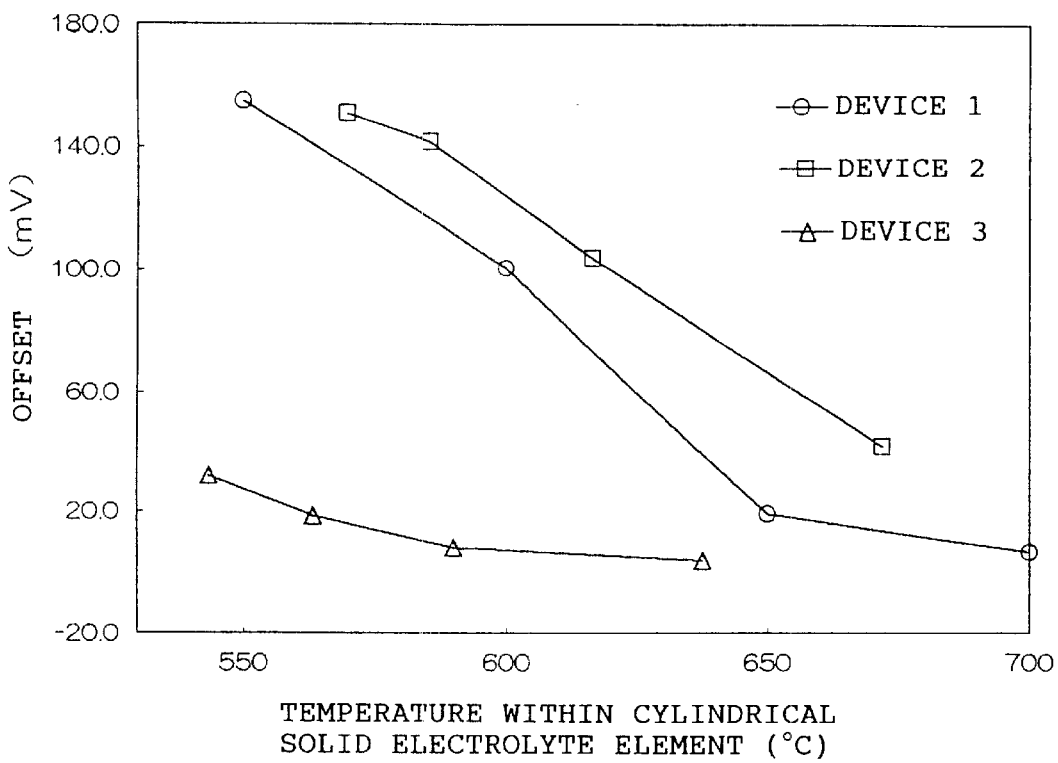
FIG. 11 is a graph showing relationship between offset and temperature within a solid electrolyte element.

As seen from FIG. 11, as compared with the device 1, in which the detection electrode contains only gold, the devices 2 and 3 exhibited a reduction in temperature dependence. Also, by employing the detection electrode of the 2-layer structure, in which the first electrode layer contains a predominant amount of platinum, temperature dependence was greatly reduced.

(2) Comparison of Oxygen Concentration Dependence among Different Electrode Components Devices 4, 5 and 6 were used for measuring combustible-gas concentration which had been manufactured according to the method described in [1] and in the following manner: device 4: the detection electrode assumes a 2-layer structure—the first electrode layer formed through platinum-plating and the second electrode layer which contains only gold; device 5: the detection electrode assumes a 2-layer structure—the first electrode layer formed through platinum-plating and the second electrode layer which contains 90 parts of gold and 10 parts of indium oxide; and device 6: the detection electrode assumes a 2-layer structure—the first electrode layer formed through platinum-plating and the second electrode layer which contains 90 parts of gold and 10 parts of iron oxide. The devices 4, 5 and 6 having different electrode components were compared in terms of oxygen concentration dependence. A gas to be measured contained propylene (500 ppmC as measured by an FID analyzer), $CO_2$ (10%), $H_2O$ (10%), $O_2$ (1, 7, or 15%), and $N_2$ (balance). The gas to be measured had a temperature of 300° C. and flowed at 15 liters/min. While the oxygen concentration of the gas being measured was varied to 1%, 7%, or 15%, the heater was electrically energized such that the internal resistance of the solid electrolyte element become 1000Ω (the surface temperature of the detection electrode became approximately 570° C.). Sensor output was measured for each of the oxygen concentration values. The results are represented by the graph of FIG. 12.

Figure 12:
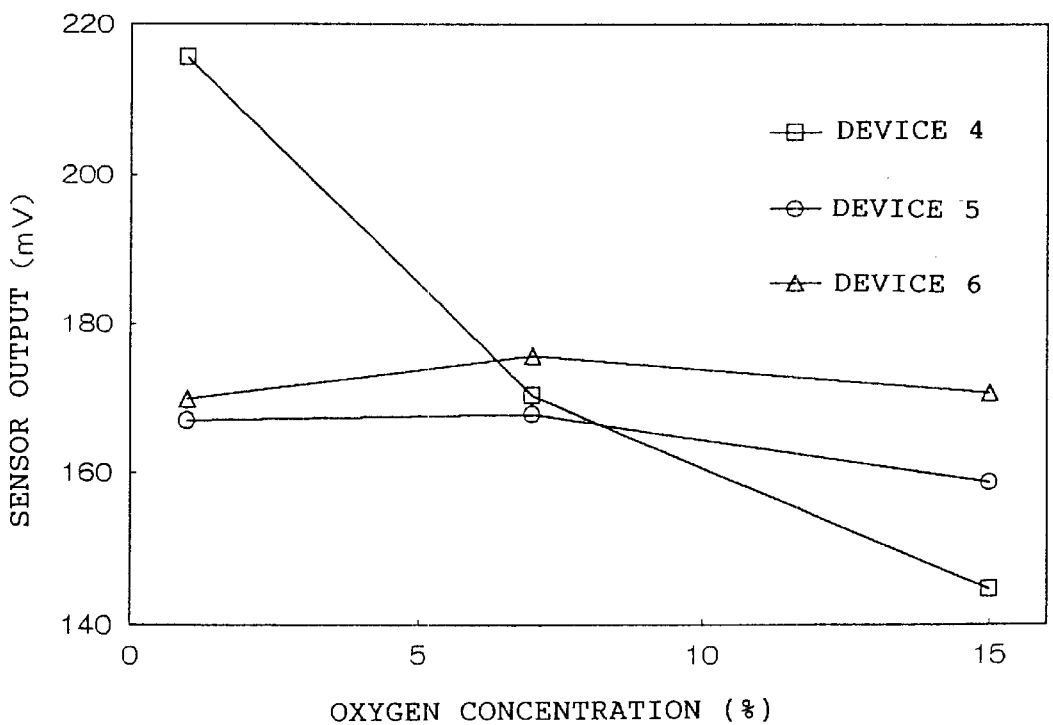
FIG. 12 is a graph showing relationship between oxygen concentration and sensor output.

As seen from FIG. 12, a metallic oxide contained in the detection electrode contributes greatly to a decrease in oxygen concentration dependence. In the case of the device 4, in which the second electrode layer contained only gold, sensor output exhibited a maximum variation of about 70 mV as a result of variations in oxygen concentration. By contrast, in the case of the devices 5 and 6, in which the second electrode layer contained a metallic oxide, variations in sensor output could be reduced to not greater than 20 mV, further to not greater than 10 mV.

(3) Comparison among Different Grain Sizes of Gold Powder Contained in Detection Electrode Closed-bottomed cylindrical solid electrolyte elements were obtained in a manner similar to that in [1]. The inner surface of each of the solid electrolyte elements was plated with platinum to thereby form a layer serving as a reference electrode. Next, a layer serving as a first electrode layer was formed on the outer surface of each of the solid electrolyte elements through platinum-plating. Each of three kinds (average grain size: 0.6 μm, 8.2 μm, 22 μm) of gold powders (90 parts) and indium oxide powder (10 parts) were mixed. To the resultant powder mixture, a binder, a dispersant, and butyl carbitol as solvent were added in respectively predetermined amounts. The obtained mixture was kneaded into paste. The paste was applied onto the platinum plating layer to thereby form a layer serving as a second electrode layer. The thus-prepared solid electrolyte elements were subjected to baking at a temperature of 880° C. for 10 minutes. Subsequently, a diffusion layer was formed; a heater element was disposed; and a reference electrode lead wire, a detection electrode lead wire, and heater element lead wires of each of the resultant solid electrolyte elements were connected to a temperature controller. Devices for measuring combustible-gas concentration were thus obtained.

Similarly, devices for measuring combustible-gas concentration in which the first electrode layer was not formed were manufactured while gold powders of three different grain sizes were used.

By using of these six kinds of devices for measuring combustible-gas concentration, measurement was carried out while a voltage of 9V was continuously applied to the heater element. A gas to be measured contained propylene (500 ppmC as measured by an FID analyzer), $O_2$ (7%), CO (10%), $H_2O$ (10%), and $N_2$ (balance). The gas to be measured had a temperature of 300° C. and flowed at 15 liters/min. The results are shown in Table 1.

TABLE 1

| Grain size of gold powder | | 0.6 μm | 8.2 μm | 22 μm |
|---|---|---|---|---|
| Sensor output (mV) | Platinum layer present | 86 | 220 | 270 |
| | Platinum layer absent | 248 | 221 | 156 |

As seen from Table 1, in the case where the first electrode layer of platinum is formed, sensitivity improves with the average grain size of gold powder. In the case of the devices for measuring combustible-gas concentration in which the first electrode layer is not formed, as the grain size decreases, sensitivity improves. Conceivably, in the case of the devices for measuring combustible-gas concentration in which the first electrode layer is formed, use of gold powder of a large grain size suppresses formation of a gold-platinum alloy, which does not generate or becomes unlikely to generate a mixed potential.

(4) Comparison of Dependence of Sensor Output on Temperature of Gas Being Measured Derived between Different Positions of Formation of Detection Electrode Devices 7 and 8 were used for measuring combustible-gas concentration which had been manufactured according to the method described in [1] such that the detection electrode assumes a 2-layer structure the first electrode layer formed through platinum-plating and the second electrode layer which contains 90 parts of gold and 10 parts of indium oxide or 10 parts of iron oxide—and as well been manufactured in the following manner: device 7: the detection electrode is formed on the entire outer surface of the solid electrolyte element; and device 8: the detection electrode is formed on the outer surface of the solid electrolyte element at only a portion extending from an end portion of the solid electrolyte element to the vicinity of the interface between a heating resistor and a heating-resistor lead portion, which are formed within the heater element contained in the cylindrical solid electrolyte element. Dependence of sensor output on temperature of a gas being measured derived from the position of the detection electrode was compared between the devices 7 and 8. This measurement used two kinds of gases to be measured—one gas to be measured contained propylene (500 ppmC), $O_2$ (7%), $CO_2$ (10%), $H_2O$ (10%), and $N_2$ (balance); and the other gas to be measured contained propylene (0 ppmC), $O_2$ (7%), $CO_2$ (10%), $H_2O$ (10%), and $N_2$ (balance). The flow rate of the gas being measured was 15 liters/min, and the temperature of the gas being measured was varied from 150° C. to 500° C. The results are plotted on the graph of FIG. 13, in which sensor output is plotted along the Y axis, and the temperature of the gas being measured is plotted along the X axis.

Figure 13:
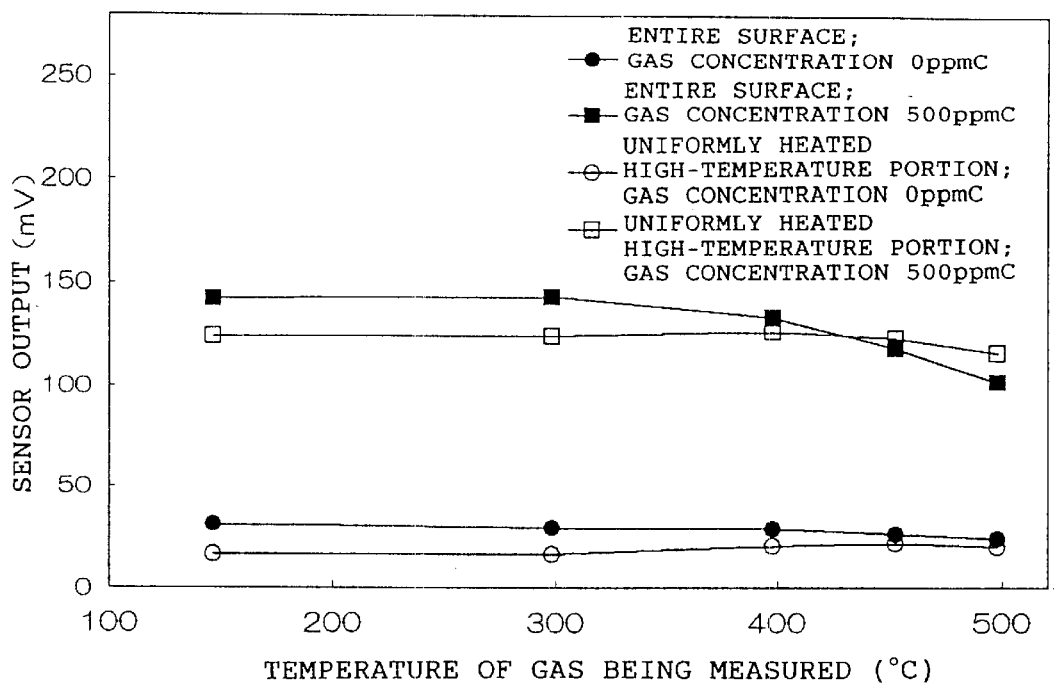
FIG. 13 is a graph showing relationship between sensor output and temperature of gas being measured.

As seen from FIG. 13, by forming the detection electrode on the outer surface of the solid electrolyte element at only a portion where high temperature is uniformly maintained, variations in sensor output caused by the temperature of the gas being measured can be suppressed. Formation of the detection electrode is particularly effective when the gas being measured contains a combustible gas (propylene) and has a temperature of not lower than 400° C.

(5) Comparison of Sensor Output among Combustible Gases

Device 9 was used for measuring combustible-gas concentration which had been manufactured according to the method described in [1] such that the detection electrode assumes a 2-layer structure—the first electrode layer formed through platinum-plating and the second electrode layer which contains 90 parts of gold and 10 parts of indium oxide. Sensor output from the device 9 was compared among combustible gases. This measurement used a gas to be measured which contained CO (10%), $H_2O$ (10%), $O_2$ (7%), and $N_2$ (balance) while the concentration of a combustible gas was varied as illustrated. The flow rate of the gas being measured was 15 liters/min, and the temperature of the gas being measured was 300° C. The results are plotted on the graph of FIG. 14, in which sensor output is plotted along the Y axis, and the concentration of a combustible gas contained in the gas being measured is plotted along the X axis.

Figure 14:
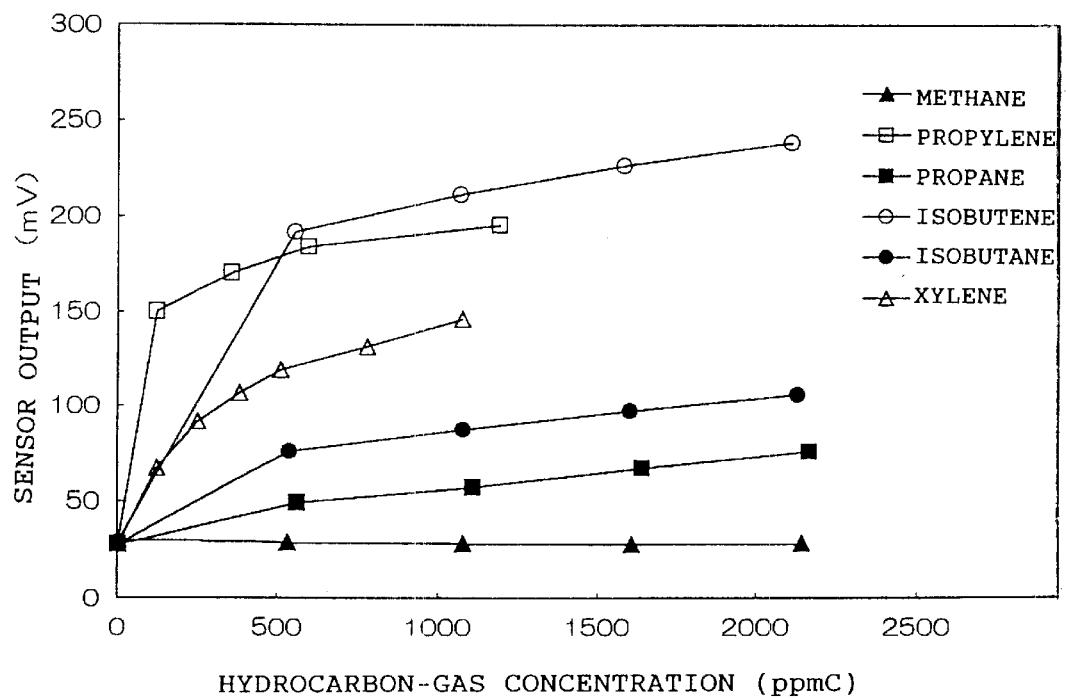
FIG. 14 is a graph showing relationship between a gas being measured and sensor output while gases being measured serve as parameters.

As seen from FIG. 14, the device of the present invention for measuring combustible-gas concentration can sufficiently detect any combustible gas. Particularly, the device can accurately measure the concentration of an unsaturated hydrocarbon having double bond, such as propylene, isobutene, or xylene and exhibits excellent response to such an unsaturated hydrocarbon.

[3] Evaluation of Diffusion Layer

A device for measuring combustible-gas concentration in which a diffusion layer contains spinel was obtained in a manner similar to that described in [1]. A solid electrolyte element on which electrodes and a diffusion layer were formed was obtained in a manner similar to that described in [1]. The solid electrolyte element was dipped in platinic chloride (0.05 g/l) aqueous solution, followed by evacuation for 10 minutes. Subsequently, the solid electrolyte element was dried at a temperature of 100° C. for at least 3 minutes, followed by firing at a temperature of 800° C. for 1 hour in the atmosphere. Then, a heater element was disposed in the solid electrolyte element such that an end portion abutted an inner bottom portion of the solid electrolyte element. Subsequently, a reference electrode lead wire, a detection electrode lead wire, and heater element lead wires were connected to a temperature controller. A device was thus obtained for measuring combustible-gas concentration in which the diffusion layer contained platinum. Similarly, a solid electrolyte element on which electrodes and a diffusion layer were formed was obtained in a manner similar to that described in [1]. The solid electrolyte element was dipped in palladium nitrate (0.05 g/l) aqueous solution, followed by subjecting to steps similar to those described above. A device was thus obtained for measuring combustible-gas concentration in which the diffusion layer contained palladium.

By using these three kinds of devices for measuring combustible-gas concentration (the device for measuring combustible-gas concentration in which the diffusion layer contains neither platinum nor palladium; the device for measuring combustible-gas concentration in which the diffusion layer contains platinum; and the device for measuring combustible-gas concentration in which the diffusion layer contains palladium), measurement was carried out while the heater element was electrically energized such that the solid electrolyte element maintained an internal resistance of 1000Ω (a surface temperature of 570° C. of the detection electrode). A gas to be measured contained propylene (1000 ppmC) or CO (1000 ppm), $O_2$ (7%), $CO_2$ (10%), $H_2O$ (10%), and $N_2$ (balance). The gas to be measured had a temperature of 300° C. and flowed at 15 liters/min. The results are shown in Table 2.

TABLE 2

| Diffusion layer | | — | Platinum-containing | Palladium-containing |
| --- | --- | --- | --- | --- |
| Sensor output (mV) | Propylene | 123.14 | 50.98 | 139.18 |
| | Carbon monoxide | 98.26 | 14.12 | 79.08 |

As seen from Table 2, the device for measuring combustible-gas concentration in which the diffusion layer contains platinum decreases sensor output for CO by 84 mV or more as compared with the device for measuring combustible-gas concentration in which the diffusion layer does not contain platinum. The reason why sensor output for CO decreases is not definitely known. It is considered that through combustion by platinum catalysis, the amount of $H_2$ and CO which reaches the detection electrode is decreased. Sensor output for propylene also decreases. However, since a decrease in sensor output for propylene is small as compared with that for, particularly, CO, sensitivity for propylene relatively increases.

The device for measuring combustible-gas concentration in which the diffusion layer contains palladium improves sensor output for propylene about 13% and decreases sensor output for CO about 20% as compared with the device for measuring combustible-gas concentration in which the diffusion layer does not contain palladium.

[4] Evaluation of Temperature Control Means

Using the device 1 (the detection electrode contains 90 parts of gold and 10 parts of indium oxide) which had been manufactured according to the method described in [1], sensor output with use of the temperature control means is compared with sensor output without use of the temperature control means. This measurement used a gas to be measured which contained $O_2$ (7%), $CO_2$ (10%), $H_2O$ (10%), and propylene (500 ppmC). The gas to be measured was tested for a temperature of 300° C. and 500° C. The flow rate of the gas being measured was 15 liters/min. In the case of the device which used the temperature control means, the internal resistance of the solid electrolyte element was controlled to 1000Ω. In the case of the device which did not use the temperature control means, voltage applied to the heater was maintained at 9 V. The results are shown in FIG. 15.

Figure 15:
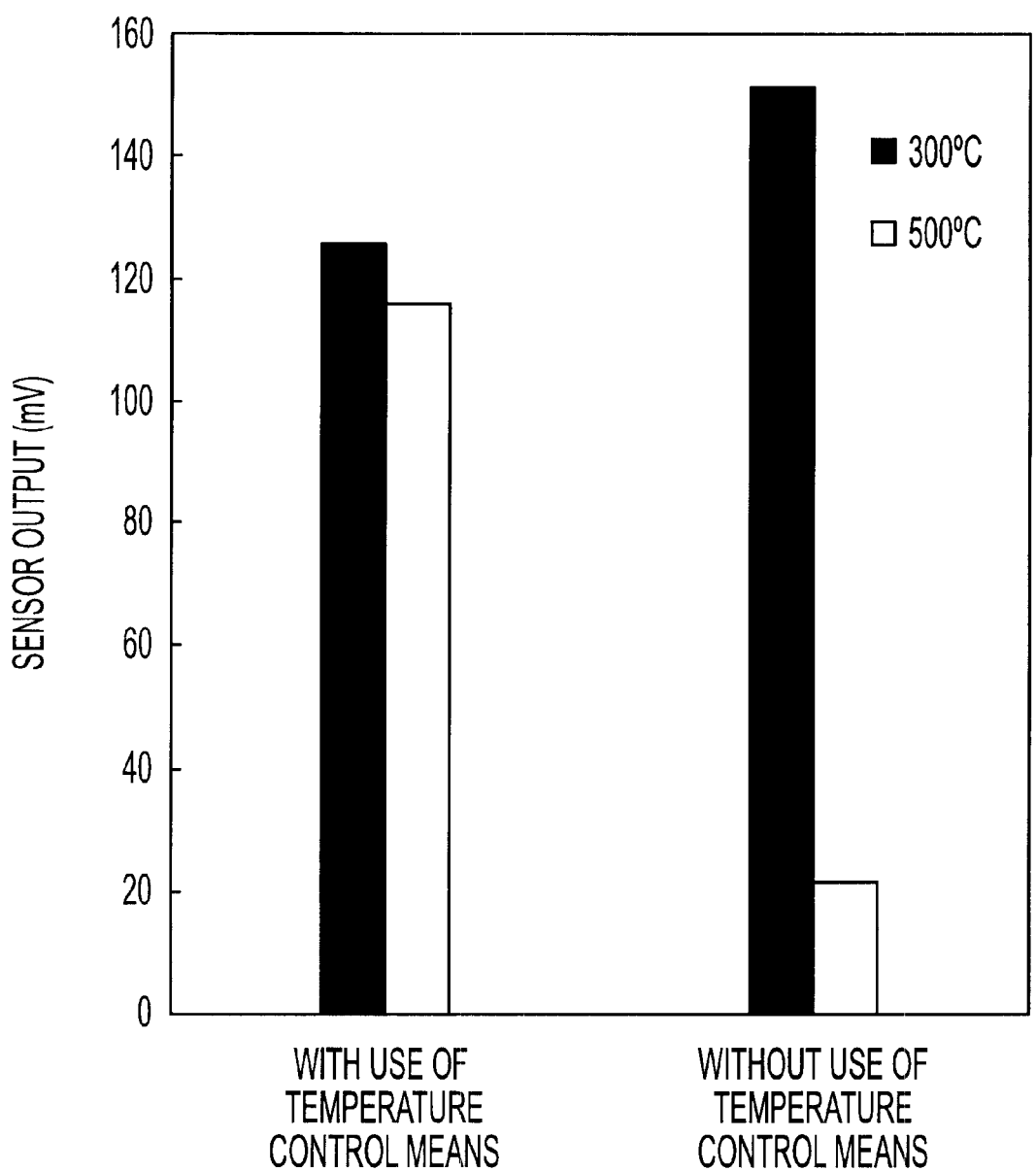
FIG. 15 is a graph showing relationship between sensor output with use of temperature control means and sensor output without use of temperature control means.

As seen from FIG. 15, in the case where the gas being measured has a temperature of 500° C. and a propylene concentration of 500 ppmC, sensor output with use of the temperature control means was 115.9 mV, whereas sensor output without use of the temperature control means was 21.8 mV, which is too small to sufficiently detect. In the case where the temperature control means is not used, a sensor output variation of about 130 mV is involved as a result of a temperature change in the gas being measured even when the concentration of propylene remains unchanged. By contrast, in the case where the temperature control means is used, a variation in sensor output derived from a variation in temperature can be suppressed to 10 mV. Thus, in the present invention, use of the temperature control means enables more sensitive detection and accurate measurement.

[5] Evaluation of Position of Heater Element

Figure 16A:
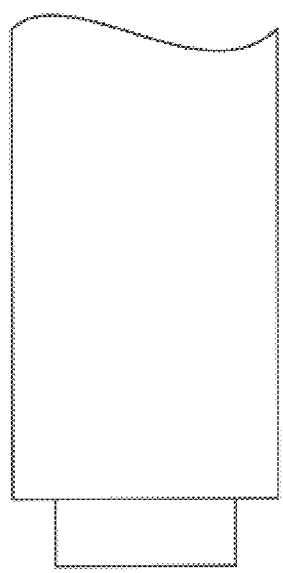
FIGS. 16A and 16B are schematic views showing an end form of a heater element used in embodiments of the invention.
Figure 16B:
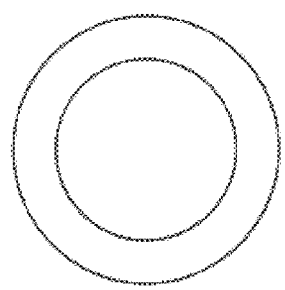
Figure 17:
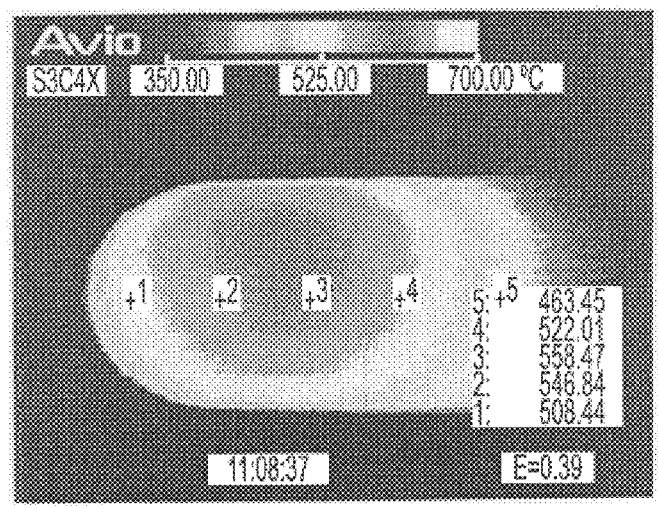
FIG. 17 is a view of temperature distribution on an upper surface of a device H1 for measuring combustible-gas concentration.
Figure 18:
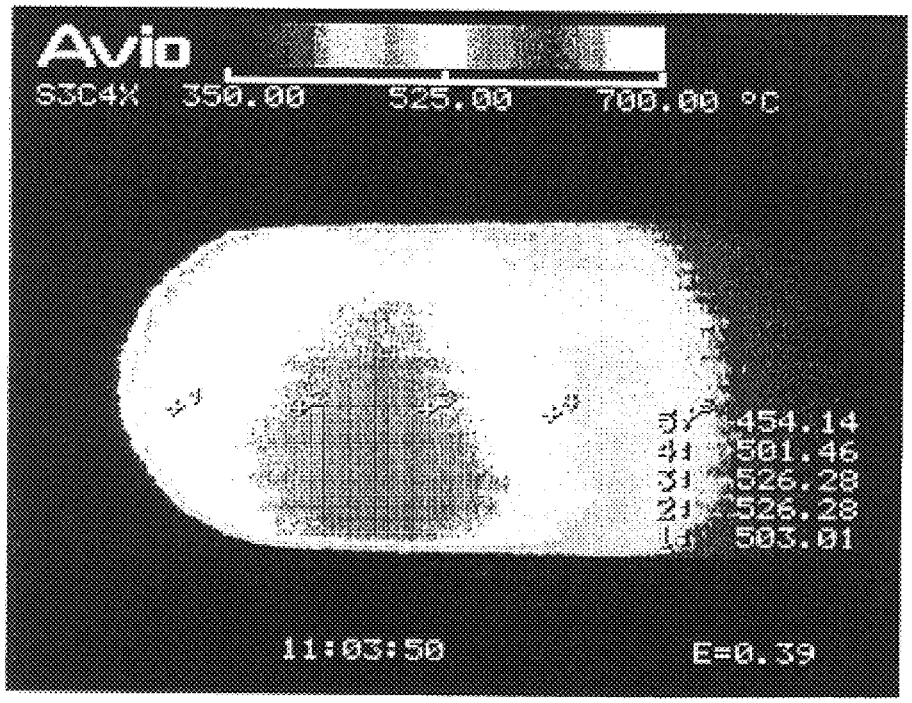
FIG. 18 is a view of temperature distribution on a right-hand side surface of the device H1 for measuring combustible-gas concentration.
Figure 19:
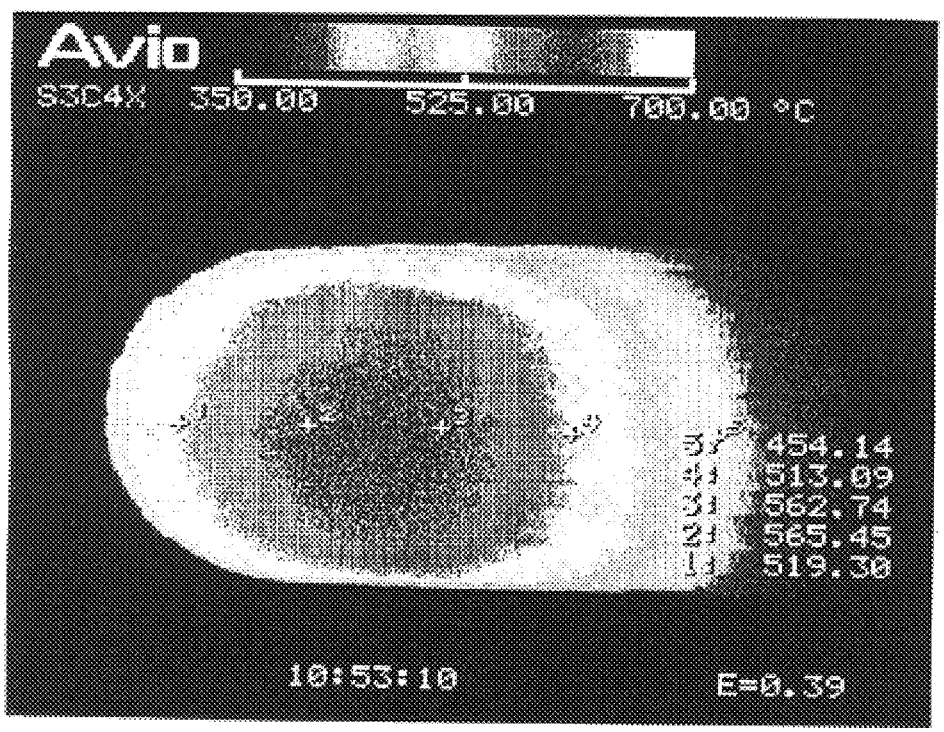
FIG. 19 is a view of temperature distribution on a lower surface of the device H1 for measuring combustible-gas concentration.
Figure 20:
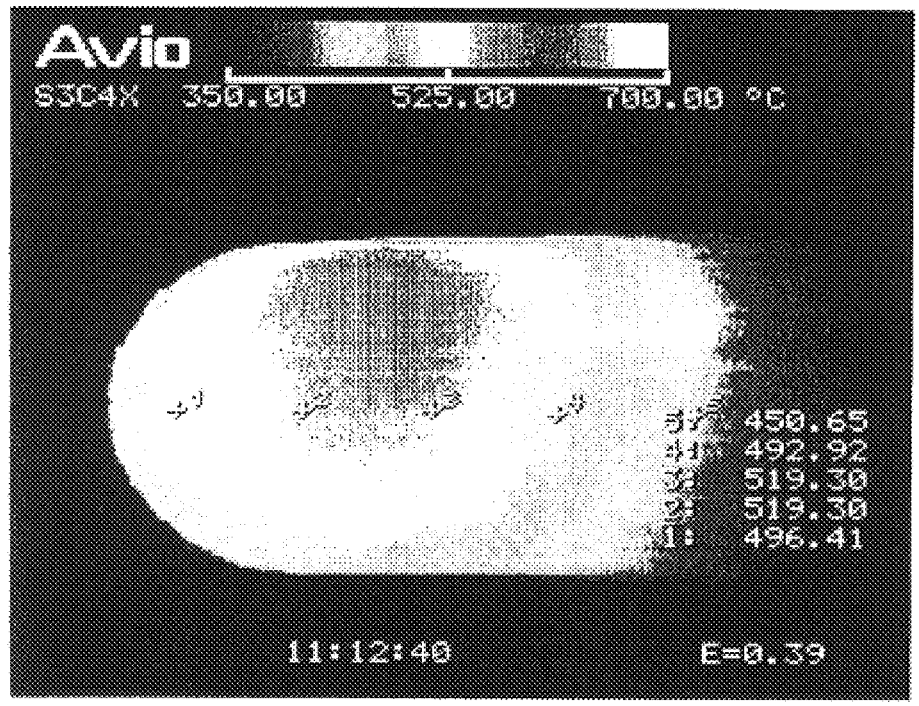
FIG. 20 is a view of temperature distribution on a left-hand side surface of the device H1 for measuring combustible-gas concentration.
Figure 21:
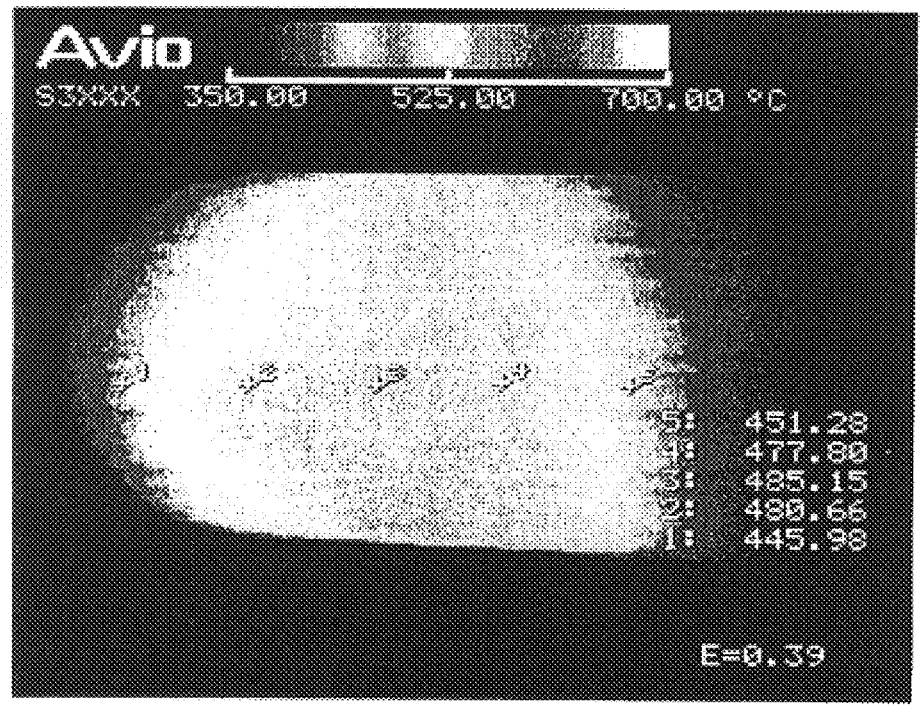
FIG. 21 is a view of temperature distribution on an upper surface of a device H2 for measuring combustible-gas concentration.
Figure 22:
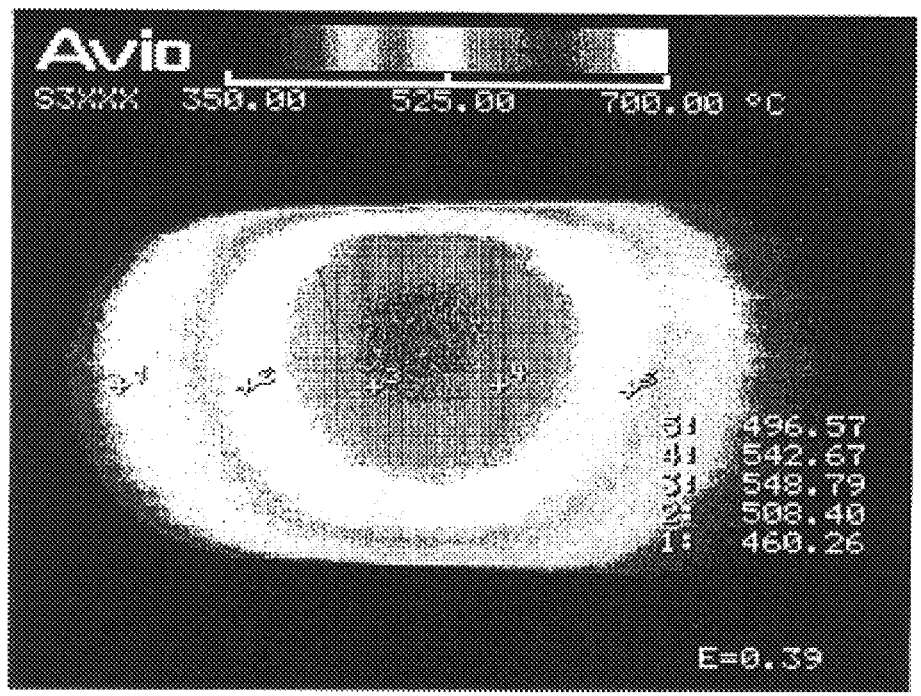
FIG. 22 is a view of temperature distribution on a right-hand side surface of the device H2 for measuring combustible-gas concentration.
Figure 23:
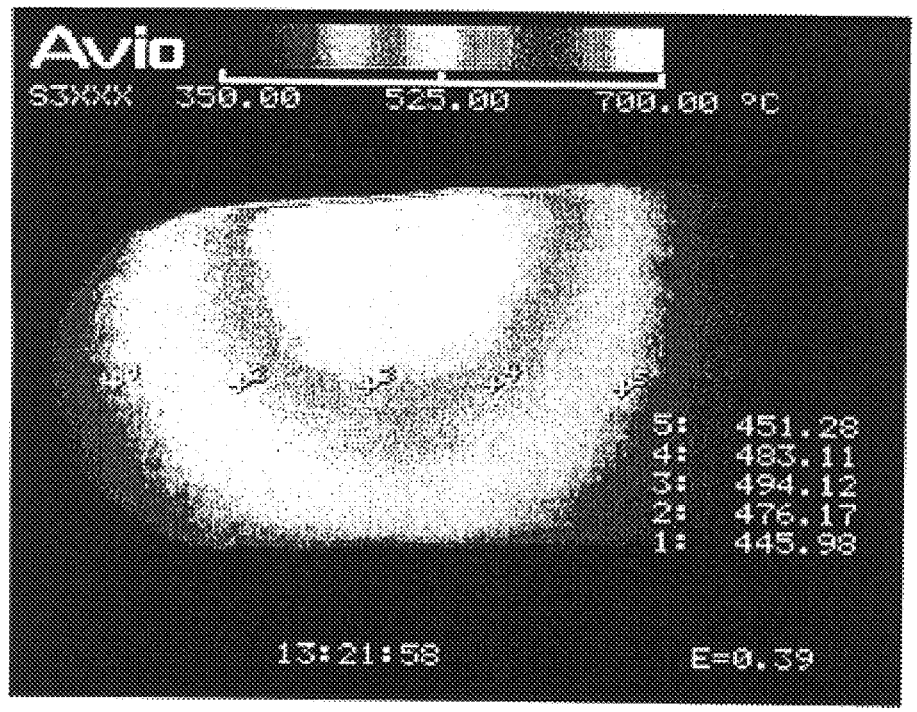
FIG. 23 is a view of temperature distribution on a lower surface of the device H2 for measuring combustible-gas concentration.
Figure 24:
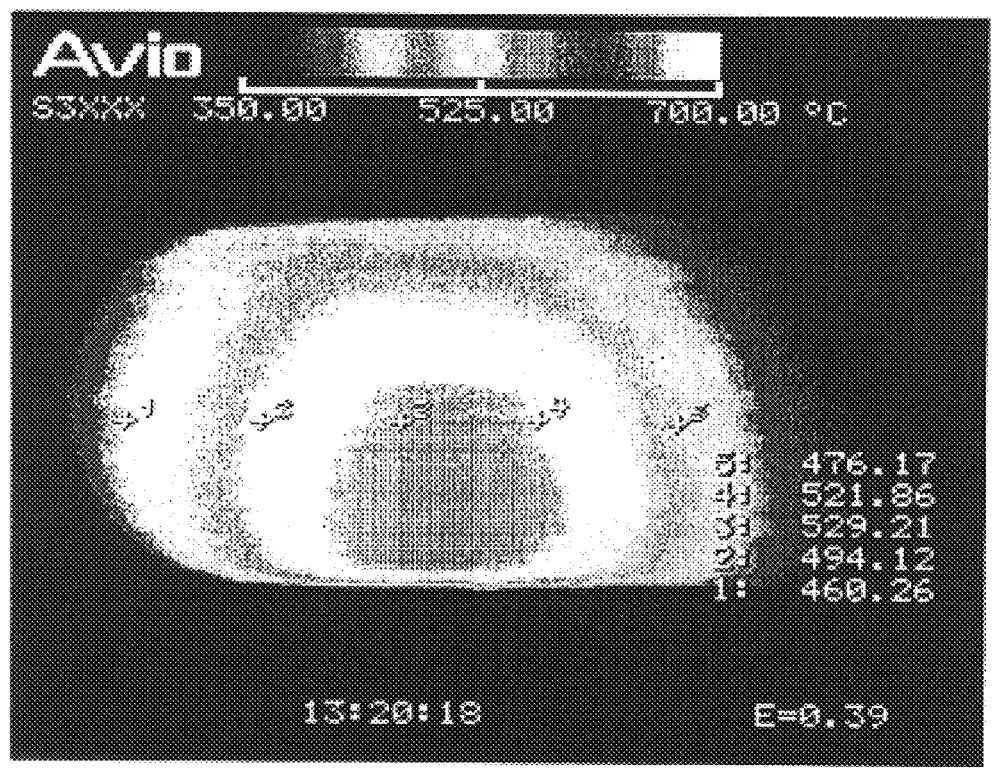
FIG. 24 is a view of temperature distribution on a left-hand side surface of the device H2 for measuring combustible-gas concentration.

Two kinds of devices were used for measuring combustible-gas concentration (the first electrode layer is formed through platinum-plating, and the second electrode layer contains 90 parts of gold and 10 parts indium oxide) which had been manufactured in a manner similar to that described in [1]. A heater element having an end form shown in FIG. 16 was disposed in the following manner: in one device, the heater element was inserted into the solid electrolyte element such that the center axis thereof coincides with the center axis of the solid electrolyte element and such that the end of the heater element is in contact with the inner surface of the bottom portion of the solid electrolyte element (hereinafter, this device for measuring combustible-gas concentration is called "H1"); and in the other device, the heater element was obliquely inserted into the solid electrolyte element such that the end portion of the heater element abutted the inner side wall of the solid electrolyte element (hereinafter, this device for measuring combustible-gas concentration is called "H2"). In H1 and H2, voltage applied to the heater element was controlled such that the internal resistance of the solid electrolyte element became 1000Ω. By use of thermography, the two kinds of devices for measuring combustible-gas concentration were measured for surface temperature at four locations which were 90 degrees apart from each other. The results are shown in FIGS. 17–24.

As seen from FIGS. 17–24, in the case of H2, a variation in temperature at point 3 is about 63° C. or more. In the case of H1, a variation in temperature is about 49° C. The maximum temperature on the surface of H2 is 548° C., whereas that of H1 is 562° C. The average value of temperatures measured at points 1–5 at all of the four locations (average temperature of 20 points) is about 486° C. in the case of H2, whereas the average temperature is as high as about 510° C. in the case of H1.

Also, as seen from FIGS. 17–24, the range of a high-temperature portion is wide in H1 and is narrow in H2. Specifically, in the case of H2, the average temperature at point 1 is about 453° C.; the average temperature at point 3 is about 514° C.; and the difference in average temperature between points 1 and 3 is 61° C. By contrast, in the case of H1, the average temperature at point 1 is about 507° C.; the average temperature at point 3 is about 542° C.; and the difference in average temperature between points 1 and 3 is 35° C. Accordingly, the temperature difference between an end portion of the device for measuring combustible-gas concentration and a portion of the device which is heated most by the heating resistor is small, and the uniformly heated high-temperature portion is held at higher temperature and exhibits uniform temperature distribution.

[6] Evaluation of Correction for Oxygen Concentration

The device for measuring combustible-gas concentration (the first electrode layer is formed through platinum-plating; the second electrode layer contains 90 parts of gold and 10 parts of indium oxide; and the diffusion layer is formed by thermal spraying of spinel) was used which had been manufactured according to the method described in [1]. Measurement was carried out while the heater element was electrically energized such that the solid electrolyte element maintained an internal resistance of 1000Ω (a surface temperature of 570° C. of the detection electrode). Gases to be measured of the following three kinds of compositions were used: propylene (530 ppmC), $O_2$ (1%, 7%, or 15%), $CO_2$ (10%), $H_2O$ (10%), and $N_2$ (balance). The gases to be measured had a temperature of 300° C. and flowed at 15 liters/min. The results are shown in Table 3.

TABLE 3

| Actual oxygen concentration | 1% | 7% | 15% |
|---|---|---|---|
| Corrected | | | |
| Sensor output (mV) | 112.4 | 114.6 | 115.1 |
| Calculated propene concentration (ppmC) | 491.5 | 530 | 540.1 |
| Uncorrected | | | |
| Sensor output (mV) | 174.1 | 114.6 | 94.9 |
| Calculated propene concentration (ppmC) | 4240.7 | 530.8 | 266.7 |

Calculation associated with "uncorrected" in Table 3 was as follows: offset at an oxygen concentration of 7% was subtracted from sensor output obtained at each oxygen concentration, and the resultant sensor output was used as one at each oxygen concentration in calculating propylene concentration. Calculation associated with "corrected" in Table 3 was as follows: offset obtained from an approximate offset curve was subtracted from sensor output obtained at each oxygen concentration, and the resultant sensor output was used as one at each oxygen concentration in calculating propylene concentration.

As a result, even though the actual concentration of propylene contained in the gas being measured was 530 ppmC, propylene concentration which was calculated on the assumption that oxygen concentration is fixed at 7% ranged from 266.7 ppmC to 4240.7 ppmC, indicating poor accuracy. By contrast, propylene concentration which is calculated after the sensor output was corrected for measured oxygen concentration ranged from 491 ppmC to 540 ppmC, which is close to the actual propylene concentration.

[7] Manufacture of Laminate-Type Device for Measuring Combustible-Gas Concentration and Device for Measuring Hydrocarbon-Gas Concentration A heater pattern serving as a heating resistor was formed between two green sheets of alumina, thereby forming a substrate serving as a heater element. A reference electrode was formed on the substrate. Previously prepared paste which contained YSZ was applied onto the reference electrode, thereby forming a layer serving as a solid electrolyte element. A platinum layer serving as a first electrode and a platinum layer serving as an internal-resistance measurement electrode were printed on the applied paste serving as a solid electrolyte element, followed by firing for integration. Subsequently, a layer serving as a second electrode layer was formed on the first electrode layer through application of paste which had been prepared by the steps of: mixing 90 parts of gold powder and 10 parts of indium oxide powder; adding to the resultant powder mixture a binder, a dispersant, and butyl carbitol as solvent in respectively predetermined amounts; and kneading the resultant mixture. The resultant laminate was subjected to firing at 880° C. for 10 minutes. Next, a diffusion layer which contained spinel was formed by thermal spraying on the surface of the second electrode layer. Then, a reference electrode lead wire, a detection electrode lead wire, and an internal-resistance measurement electrode lead wire were connected to temperature control means, thereby providing a laminate-type device for measuring combustible-gas concentration. Similarly, a device for measuring hydrocarbon-gas concentration was obtained. These devices have the capabilities for sensitive detection and accurate measurement while exhibiting low dependence on oxygen concentration as well as on the temperature of a gas to be measured, as in the case of the device for measuring combustible-gas concentration which includes a closed-bottomed cylindrical solid electrolyte element.

The device of the first aspect of the invention for measuring combustible-gas concentration can sensitively detect a combustible gas contained in a gas being measured and can accurately measure the concentration of the combustible gas, and as well can suppress dependence on the concentration of oxygen contained in the gas being measured to a very low level. The devices of the second and third aspects of the invention for measuring combustible-gas concentration can accurately carry out detection and measurement while suppressing offset to a low level and exhibiting low dependence on the temperature of a gas being measured. The device of the thirteenth aspect of the invention for measuring hydrocarbon-gas concentration can sensitively detect a hydrocarbon gas contained in a gas being measured and can accurately measure the concentration of the hydrocarbon gas, and as well can suppress dependence on the concentration of oxygen contained in the gas being measured to a very low level. The devices of the fourteenth and fifteenth aspects of the invention for measuring hydrocarbon-gas concentration can accurately carry out detection and measurement while suppressing offset to a low level and exhibiting low dependence on the temperature of a gas being measured. The method of the twenty-fifth aspect of the invention for measuring combustible-gas concentration and the method of the twenty-sixth aspect of the invention for measuring hydrocarbon-gas concentration can measure the concentration of a target gas in a particularly accurate manner.

While the invention has been described in detail and with reference to specific embodiments thereof, it will be apparent to one skilled in the art that various changes and modifications can be made therein without departing from the spirit and scope thereof.

This application is based on Japanese Patent Application Nos. Hei. 11-164520 filed Jun. 10, 1999 and Hei. 11-219351 filed Aug. 2, 1999, which are incorporated herein by reference in their entirety.

What is claimed is:

1. A device for measuring combustible-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant, wherein the detection electrode contains gold and a metallic oxide; and the detection electrode is formed on the solid electrolyte element only at a portion corresponding to a heating resistor formed within the heater element.

2. The device for measuring combustible-gas concentration as claimed in claim 1, wherein the detection electrode contains gold and a metallic oxide selected from the group consisting of an oxide of at least one of In, Fe, Ta, Ga, Sr, Eu, W, Ce, Ti, Zr and Sn and mixtures thereof.

3. The device for measuring combustible-gas concentration as claimed in claim 1, wherein the detection electrode contains gold and at least one of indium oxide and iron oxide.

4. The device as claimed in claim 1, for measuring hydrocarbon concentration.

5. The device as claimed in claim 1, for measuring ammonia concentration.

6. The device as claimed in claim 1, for measuring one or both of hydrocarbon and ammonia concentration contained in an exhaust gas emitted from a lean-burn engine.

7. A device for measuring combustible-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant, wherein the detection electrode comprises a first electrode layer formed on the surface of the solid electrolyte element and a second electrode layer formed on a surface of the first electrode layer; the first electrode layer containing at least one metal selected from the group consisting of platinum and gold; the second electrode layer containing at least one component selected from the group consisting of gold and a metallic oxide, wherein the first electrode layer has a composition that is different from that of the second electrode layer; and the detection electrode is formed on the solid electrolyte element only at a portion corresponding to a heating resistor formed within the heater element.

8. A device for measuring combustible-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant, wherein the detection electrode comprises a first electrode layer formed on the surface of the solid electrolyte element, a second electrode layer formed on a surface of the first electrode layer, and a third electrode layer formed on a surface of the second electrode; the first electrode layer containing a predominant amount of platinum; the second electrode layer containing a predominant amount of gold; the third electrode layer containing a metallic oxide; and the detection electrode is formed on the solid electrolyte element only at a portion corresponding to a heating resistor formed within the heater element.

9. A device for measuring combustible-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling the voltage applied to the heater element such that the internal resistance becomes constant,
    wherein the detection electrode contains gold and is formed on the solid electrolyte element only at a portion extending from an end portion of the solid electrolyte element to the vicinity of an interface between a heating resistor and a heating-resistor lead portion, which are formed within the heater element; the solid electrolyte element has the form of a closed-bottomed cylinder; the heater element disposed within the solid electrolyte element has a rod form; the central axis of the solid electrolyte element and the central axis of the heater element substantially coincide with each other; and at least a portion of an end of the heater element is in contact with an inner surface of a bottom portion of the solid electrolyte element.

10. The device for measuring combustible-gas concentration as claimed in claim 9, wherein the detection electrode contains gold and a metallic oxide.

11. A device for measuring combustible-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant,
    wherein the detection electrode comprises a first electrode layer formed on a surface of the solid electrolyte element and a second electrode layer formed on a surface of the first electrode layer, the first electrode layer containing platinum; the second electrode layer containing gold; the second electrode layer is formed from paste containing gold powder of an average grain size of 1–100 μm by baking the paste; the detection electrode is formed on the solid electrolyte element only at a portion extending from an end portion of the solid electrolyte element to the vicinity of an interface between a heating resistor and a heating resistor lead portion, which are formed within the heater element; the solid electrolyte element has the form of a closed-bottom cylinder; the heat element disposed within the solid electrolyte element has a rod form; the central axis of the solid electrolyte element and the central axis of the heater element substantially coincide with each other; and at least a portion of an end of the heater element is in contact with an inner surface of the bottom portion of the solid electrolyte element.

12. A device for measuring hydrocarbon-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant,
    wherein the detection electrode contains gold and a metallic oxide; and the detection electrode is formed on the solid electrolyte element only at a portion corresponding to a heating resistor formed within the heater element.

13. A device for measuring hydrocarbon-gas concentration, comprising an oxygen-ion-conductive solid electrolyte element, a reference electrode, a detection electrode formed on a surface of the solid electrolyte element, and a diffusion layer containing Pd formed on a surface of the detection electrode, and a heater element for heating the solid electrolyte element, means for periodically measuring the internal resistance of the solid electrolyte element, and temperature control means for controlling a voltage applied to the heater element such that the internal resistance becomes constant,
    wherein the detection electrode comprises a first electrode layer formed on the surface of the solid electrolyte element and a second electrode layer formed on a surface of the first electrode layer; the first electrode layer containing at least one metal selected from the group consisting of platinum and gold; the second electrode layer containing at least one component selected from the group consisting of gold and a metallic oxide, wherein the first electrode layer has a composition that is different from that of the second electrode layer; and the detection electrode is formed on the solid electrolyte element only at a portion corresponding to a heating resistor formed within the heater element.

14. A device for measuring hydrocarbon-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling a voltage applied to the heater element such that the internal resistance becomes constant,
    wherein the detection electrode comprises a first electrode layer formed on the surface of the solid electrolyte element, a second electrode layer formed on a surface of the first electrode layer, and a third electrode layer formed on a surface of the second electrode; the first electrode layer containing a predominant amount of platinum; the second electrode layer containing a predominant amount of gold; the third electrode layer containing a metallic oxide; and the detection electrode is formed on the solid electrolyte element only at a portion corresponding to a heating resistor formed within the heater element.

15. A device for measuring hydrocarbon-gas concentration, comprising an oxygen-ion-conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of a solid electrolyte element, and temperature control means for controlling a voltage applied to the heater element such that the internal resistance becomes constant, wherein the detection electrode contains gold and is formed on the solid electrolyte element only at a portion extending from an end portion of the solid electrolyte element to the vicinity of an interface between a heating resistor and a heating-resistor lead portion, which are formed within the heater element; the solid electrolyte element has the form of a closed-bottomed cylinder; the heater element disposed within the solid electrolyte element has a rod form; the central axis of the solid electrolyte element and the central axis of the heater element substantially coincide with each other; and at least a portion of an end of the heater element is in contact with an inner surface of a bottom portion of the solid electrolyte element.

16. The device for measuring hydrocarbon-gas concentration as claimed in claim 15, wherein the detection electrode contains gold and a metallic oxide.

17. A device for measuring hydrocarbon-gas concentration, comprising an oxygen-ion conductive solid electrolyte element, a reference electrode, a detection electrode formed on a surface of the solid electrolyte element, and a diffusion layer containing Pd formed on a surface of the detection electrode, a heater element for heating the solid electrolyte element, means for periodically measuring the internal resistance of the solid electrolyte element, and temperature control means for controlling the voltage applied to the heater element such that the internal resistance becomes constant, wherein the detection electrode comprises a first electrode layer formed on a surface of the solid electrolyte element and a second electrode layer formed on a surface of the first electrode layer; the first electrode layer containing platinum; the second electrode layer containing gold; the second electrode layer is formed from paste containing gold powder of an average grain size of 1–100 $\mu$m and by baking the paste; the detection electrode is formed on the solid electrolyte element only at a portion extending from an end portion of the solid electrolyte element to the vicinity of an interface between a heating resistor and a heating-resistor lead portion, which are formed within the heater element; the solid electrolyte element has the form of a closed-bottom cylinder; the heater element disposed within the solid electrolyte element has a rod form; the central axis of the solid electrolyte element and the central axis of the heater element substantially coincide with each other; and at least a portion of an end of the heater element is in contact with an inner surface of the bottom portion of the solid electrolyte element.

* * * * *